US008735595B2

(12) United States Patent
Gu et al.

(10) Patent No.: US 8,735,595 B2
(45) Date of Patent: May 27, 2014

(54) ACETYL-COA CARBOXYLASE (ACC) INHIBITORS AND THEIR USE IN DIABETES, OBESITY AND METABOLIC SYNDROME

(75) Inventors: Yu Gui Gu, Libertyville, IL (US); Xiangdong Xu, Buffalo Grove, IL (US); Moshe Weitzberg, Highland Park, IL (US); Hing L. Sham, South San Francisco, CA (US)

(73) Assignee: AbbVie Inc., North Chicago, IL (US)

( * ) Notice: Subject to any disclaimer, the term of this patent is extended or adjusted under 35 U.S.C. 154(b) by 1652 days.

(21) Appl. No.: 11/675,406

(22) Filed: Feb. 15, 2007

(65) Prior Publication Data

US 2007/0219251 A1 Sep. 20, 2007

Related U.S. Application Data

(60) Provisional application No. 60/773,514, filed on Feb. 15, 2006.

(51) Int. Cl.
*A61K 31/4439* (2006.01)
*A61K 31/426* (2006.01)
*C07D 417/04* (2006.01)
*C07D 277/34* (2006.01)

(52) U.S. Cl.
USPC ......... 548/182; 546/270.4; 514/342; 514/369

(58) Field of Classification Search
USPC ....................................... 548/182; 546/270.4
See application file for complete search history.

(56) References Cited

U.S. PATENT DOCUMENTS

| 4,720,493 | A | 1/1988 | Kawakita et al. | |
| 5,177,067 | A * | 1/1993 | Guerry et al. | 514/183 |
| 5,750,470 | A | 5/1998 | Morimoto et al. | |
| 5,760,032 | A | 6/1998 | Kitajima et al. | |
| 6,441,177 | B1 * | 8/2002 | Aebi et al. | 546/193 |
| 6,586,453 | B2 * | 7/2003 | Dhanoa et al. | 514/365 |
| 6,620,828 | B2 | 9/2003 | Chu et al. | |
| 6,979,741 | B2 | 12/2005 | Perry et al. | |
| 7,928,243 | B2 | 4/2011 | Gu et al. | |
| 8,207,350 | B2 | 6/2012 | Gu et al. | |
| 2004/0176409 | A1 | 9/2004 | McGee et al. | |
| 2005/0203146 | A1 | 9/2005 | Herpin et al. | |
| 2005/0288340 | A1 | 12/2005 | Hamanaka | |
| 2007/0225332 | A1 | 9/2007 | Gu et al. | |
| 2009/0239830 | A1 | 9/2009 | Munger et al. | |

FOREIGN PATENT DOCUMENTS

| CA | 2521830 A1 * | 10/2004 |
| EP | 1553091 | 7/2005 |
| GB | 2404855 | 2/2005 |
| JP | 59-196876 | 10/2005 |
| JP | 2006022065 | 1/2006 |
| WO | 96/04278 | 2/1996 |
| WO | 97/12879 | 4/1997 |
| WO | 98/08845 | 3/1998 |
| WO | 02/051355 | 7/2002 |
| WO | 02/100403 | 12/2002 |
| WO | 03/009841 | 2/2003 |
| WO | WO-03/015773 A2 * | 2/2003 |
| WO | 03/072100 | 9/2003 |
| WO | WO-2004/052840 A1 * | 6/2004 |
| WO | 2004/106307 | 12/2004 |
| WO | 2004/113331 | 12/2004 |
| WO | 2005/007647 | 1/2005 |
| WO | 2005/044793 | 5/2005 |
| WO | 2005/051945 | 6/2005 |
| WO | WO-2005/063729 A1 * | 7/2005 |
| WO | 2005/070920 | 8/2005 |
| WO | 2005/113069 | 12/2005 |
| WO | 2006/002099 | 1/2006 |
| WO | WO-2006/011631 A2 * | 2/2006 |

OTHER PUBLICATIONS

El Kazzouli et al., Journal Marocain de Chimie Heterocyclique (Dec. 2004), 3(1), pp. 1-7.*
Brown et al., Journal of the Chemical Society, 1954, pp. 873-880.*
Turkoglu et al., "Effect of Abdominal Obesity on Insulin Resistance and the Components of the Metabolics Syndrome: Evidence Supporting Obesity as the Central Feature" Obes. Surg. 13: 699-705 (2003).
Steyn et al., "Diet, Nutrition and the Prevention of Type 2 Diabetes" Public Health Nutr. 7: 146-165 (2004).
Hulver et al., "Skeletal Muscle Lipid Metabolism with Obesity" Am. J. Physiol. Endocrinol Metab. 284: E741-747 (2003).
Sinha, et al., "Assessment of Skeletal Muscle Triglyceride Content by 1H Nuclear Magnetic Resonance Spectroscopy in Lean and Obese Adolescents: Relationships to Insulin Sensitivity, Total Body Fat, and Central Adiposity" Diabetes 51: 1022-1027 (2002).
Friedman et al., "Fat in All the Wrong Places" Nature 415: 268-269 (2002).
Ruderman et al., "AMP Kinase and Malonyl-CoA: Targets for Therapy of the Metabolic Syndrome" Nature Rev. Drug Discov. 3: 340-351 (2004).
Mao et al., "Human Acetyl-CoA Carboxylase 1 Gene: Presence of Three Promoters and Heterogeneity at the 5-untranslated mRNA Region" Proc. Natl. Acad. Sci. USA 100: 7515-7520 (2003).
Abu-Elheiga et al., "Human Acetyl-CoA Carboxylase 2: Molecular Cloning, Characterization, Chromosomal Mapping, and Evidence for Two Isoforms" J. Biol. Chem. 272: 10669-10699 (1997).
Wade, L.G., Jr., Organic Chemistry, 3rd ed., Chapter 13 entitled "Ethers and Epoxides," p. 594; Chapter 18 entitled "Ketones and Aldehydes," p. 810; Chapter 19 entitled "Structure of Amines," p. 871; and Chapter 19 entitled: "Basicity of Amines," p. 879, Dec. 22, 1994.

(Continued)

*Primary Examiner* — Laura L. Stockton
(74) *Attorney, Agent, or Firm* — Lisa V. Mueller; Michael Best & Friedrich LLP

(57) ABSTRACT

The present invention relates to compounds of formula (I)

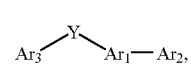

(I)

which inhibit acetyl-CoA carboxylase (ACC) and are useful for the prevention or treatment of metabolic syndrome, type II diabetes, obesity, atherosclerosis and cardiovascular diseases in humans.

16 Claims, No Drawings

(56) References Cited

OTHER PUBLICATIONS

Aicher, T.D. et al., "Substituted tetrahydropyrrolo[2,1-b]oxazol-5(6H)—ones and tetrahydropyrrolo[2,1-b]thiazol-5(6H)—ones as hypoglycemic agents," J. Med. Chem. (1998) 41(23):4556-4566.
Chemical Abstracts Registry No. 52170-13-5, indexed in the Registry file on STN Nov. 16, 1984.
Friedman et al., "Fat in all the wrong places," Nature (2002) 415:268-269.
United States Patent Office Action for U.S. Appl. No. 11/950,692, dated Aug. 2, 2010 (17 pages).
United States Patent Office Action for U.S. Appl. No. 12/259,090, dated Jun. 13, 2011 (9 pages).
United States Patent Office Action for U.S. Appl. No. 11/675,410, dated May 24, 2010 (11 pages).
United States Patent Office Action for U.S. Appl. No. 11/675,410, dated Jan. 4, 2011 (8 pages).
United States Patent Office Action for U.S. Appl. No. 11/675,410, dated Jun. 8, 2011 (7 pages).
United States Patent Office Action for U.S. Appl. No. 11/675,410, dated Jul. 9, 2013 (21 pages).
United States Patent Office Notice of Allowance for U.S. Appl. No. 11/675,410, dated Oct. 24, 2013 (14 pages).

* cited by examiner

ACETYL-COA CARBOXYLASE (ACC) INHIBITORS AND THEIR USE IN DIABETES, OBESITY AND METABOLIC SYNDROME

CROSS-REFERENCE SECTION TO RELATED APPLICATIONS

This application claims the benefit of priority of U.S. Provisional Application Ser. No. 60/773,514, which was filed Feb. 15, 2006, and is incorporated herein by reference in its entirety.

FIELD OF THE INVENTION

The present invention relates to compounds, which inhibit acetyl-CoA carboxylase (ACC) and are useful for the prevention or treatment of metabolic syndrome, type 2 diabetes, obesity, atherosclerosis and cardiovascular diseases in humans.

BACKGROUND OF THE INVENTION

The incidence of type 2 diabetes has dramatically increased over the past decade. This epidemic is largely attributed to proliferation of key risk factors, which include a sedentary lifestyle, a high fat diet, obesity and the demographic shift to a more aged population. There is ample evidence to indicate that increased abdominal obesity and physical inactivity contribute significantly to the development of type 2 diabetes (Turkoglu C, Duman B S, Gunay D, Cagatay P, Ozcan R, Buytikdevrim A S: Effect of abdominal obesity on insulin resistance and the components of the metabolic syndrome: evidence supporting obesity as the central feature. Obes Surg 2003; 13: 699-705. Steyn N P, Manii J, Bennett P H, Temple N, Zimmet P, Tuomileito J, Lindstrom X, Louheranta A: Diet, nutrition and the prevention of type 2 diabetes. Public Health Nutr 2004; 7: 147-65).

At the cellular level, an increase in ectopic fat storage in nonadipose tissues such as in muscle, liver and pancreas is a strong predictor of the development of insulin resistance and type 2 diabetics (Hulver M W, Berggren J R, Cortrighit R N, Dudek R W, Thompson R P, Pories W J, MacDonald K G, Cline G W, Shulman G I, Dohm C L, Houmard J A: Skeletal muscle lipid metabolism with obesity. Am J Physiol Endocrinol Metab 2003; 284: E741-7. Sinha R, Dufour S, Petersen K F, LeBon V, Enoksson S, Ma Y Z, Savoye M, Rothlman D L, Shulman G I, Caprio S: Assessment of skeletal muscle triglyceride content by $^1$H nuclear magnetic resonance spectroscopy in lean and obese adolescents: relationships to insulin sensitivity, total body fat, and central adiposity, Diabetes 2002; 51: 1022-7). The precise mechanism of how increased intracellular lipid content exacerbates whole body insulin sensitivity is unclear at present but it has been postulated that increased long chain fatty acyl-CoAs, ceramide or diacylglycerol, whose contents are proportional to the accumulation of intramyocellular triglyceride, antagonizes metabolic actions of insulin, reduces muscle glucose uptake and inhibits hepatic glucose production (Sinha R, Dufour S, Petersen K F, LeBon V, Enoksson S, Ma Y Z, Savoye M, Rothman D L, Shulman G I, Caprio S: Assessment of skeletal muscle triglyceride content by $^1$H nuclear magnetic resonance spectroscopy in lean and obese adolescents: relationships to insulin sensitivity, total body fat, and central adiposity. Diabetes 2002; 51: 1022-7 Friedman J: Fat in all the wrong places. Nature 2002; 415: 268-9). As muscle is the primary site of metabolic action of insulin, the development of muscle insulin resistance along with liver insulin resistance are thus inherently linked to the development of whole body insulin resistance.

In order to increase muscle and liver fat oxidation and thus limit the concentration of LCFACoA's we aim to inhibit the activity of Acetyl CoA Carboxylase (ACC), which catalyzes the production of malonyl-CoA from acetyl-CoA. Malonyl-CoA is an intermediate substrate that plays an important role in the overall fatty acid metabolism: Malonyl-CoA is utilized by fatty acid synthase for de novo lipogenesis, and also acts as a potent allosteric inhibitor of carniitine palmitoyltransferase 1 (CPT1), a mitochondrial membrane protein that shuttles long chain fatty acyl CoAs into the mitochondrial where they are oxidized (Ruderman N, Prentki M: AMP kinase and malonyl-CoA: targets for therapy of the metabolic syndrome Nat Rev Drug Discov 2004; 3: 340-511) A small molecule inhibitor of ACC would thus limit de novo lipid synthesis, dce-inhibit CPT1 and subsequently increase fat oxidation.

In rodents and in humans, there are two known isoforms of ACC that are encoded by distinct genes and share approximately 70% amino acids identity. ACC1, which encodes a 265 KD protein, is highly expressed in the cytosol of lipogenic tissues such as liver and adipose, whereas 280 KD ACC2 protein is preferentially expressed in oxidative tissues, skeletal muscle and heart (Mao J, Chirala S S, Wakil S J: Human acetyl-CoA carboxylase 1 gene: presence of three promoters and heterogeneity at the 5'-untranslated mRNA region. Proc Natl Acad Sci USA 2003; 100: 7515-20. Abu-Elheiga L, Almarza-Ortega D B, Baldini A, Wakil S J: Human acetyl-CoA carboxylase 2, Molecular cloning, characterization, chromosomal mapping, and evidence for two isoforms. J Biol Chem 1997; 272: 10669-77). ACC2 has a unique 114 amino acid N-terminus with a putative transmembrane domain (TM), which is thought to be responsible for mitochondrial targeting (Abu-Ellheiga L, Brinkley W R, Zhong L, Chirala S S, Woldegiorgis C, Wakil S J: The subcellular localization of acetyl-CoA carboxylase 2. Proc Natl Acad Sci USA 2000; 97: 1444-9). Based on tissue distribution and subcellular localization of these two isoforms, the current hypothesis is that a distinct pool of Malonyl-CoA produced by ACC1 is preferentially converted into fatty acids by fatty acid synthase, whereas another pool of Malonyl-CoA synthesized primarily by ACC2, presumed localized in near mitochondria, can be involved in the inhibition of CPT1 (Abu-Elheiga L, Brinkley W R, Zhong L, Chirala S S, Woldegiorgis G, Wakil S J: The subcellular localization of acetyl-CoA carboxylase 2. Proc Natl Acad Sci USA 2000; 97: 1444-9). Therefore, ACC1 inhibition reduces fatty acid synthesis and can be beneficial for use in treating diseases such as metabolic syndrome.

Genetic studies have demonstrated that ACC2 knockout mice are healthy and fertile with a favorable metabolic phenotype, increased fatty acid oxidation, increased thermogenesis, reduced hepatic TG content and subsequent decrease in body weight despite increase in food intake compared to their littermates (Abu-Elheiga Lt, Matzuk M M, Abo-Hashema K A, Wakil S J: Continuous fatty acid oxidation and reduced fat storage in mice lacking acetyl-CoA carboxylase 2. Science 2001; 291: 2613-6). In addition, these mice are resistant against high fat diet-induced obesity and insulin resistance (Abu-Elheiga L, Oh W, Kordari P, Wakil S J: Acetyl-CoA carboxylase 2 mutant mice are protected against obesity and diabetes induced by high-fat/high-carbohydrate diets. Proc Natl Acad Sci USA 2003; 100: 10207-12). Also, recently it was demonstrated that the effects of leptin and adiponectin, cytokines secreted from adipose tissue, to increase fatty acid oxidation are at least due in part to the inhibition of ACC in liver and skeletal muscle (Yamauchi T, Kamon J, Waki H, Terauclhi Y, Kubota N, Hara K, Mori Y, Ide T, Murakami I C, Tsuboyama-ICasaoka N, Ezaki O, Akanuma Y, Gavrilova O, Vinson C, Reitman M L, Kagechika H, Shudo K, Yoda M, Nakano Y, Tobe K, Nagai R, Kimura S, Tomita M, Froguel P, Kadowaki T: The fat-derived hormone adiponectin reverses insulin resistance associated with both lipoatrophy and obesity, Nat Med 2001; 7: 941-6). Taken together these data support that the discovery of small molecular inhibitors of ACC2 can provide a favorable metabolic profile against obesity induced type 2 diabetic patients, Furthermore, the dual inhibition of ACC1 and ACC2 can provide the profile needed to demonstrate benefit for patients exhibiting conditions of metabolic syndrome.

SUMMARY OF THE INVENTION

The present invention is directed to compounds of formula (I),

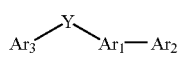

(I)

or a pharmaceutically acceptable salt, prodrug, salt of a prodrug, or combination thereof, wherein Y is selected from the group consisting of —$CR_xR_y$—, —C(O)—, —O—, —N(H)—, —N(alkyl)- and —S—; wherein each of $R_x$ and $R_y$ is independently selected from the group consisting of hydrogen, alkyl, hydroxyalkyl, and haloalkyl; or $R_x$, and $R_y$ together with the carbon to which they are attached form a monocyclic cycloallyl or heterocycle ring;

$Ar_1$ is selected from the group consisting of phenyl and a monocyclic, five or six-membered heteroaryl;

$Ar_3$ is phenyl or monocyclic heteroaryl; wherein $Ar_3$ is substituted with 1, 2, 3 or 4 substituents independently selected from the group consisting of alkyl, alkenyl, —CN, —$NO_2$, halogen, —$OR_2$, —O—N=$CH(R_1)$, —$OC(O)R_1$, —$OC(O)N(R_3)(R_2)$, —$OC(O)OR_1$, —$OS(O)_2R_1$, —$SR_2$, —$S(O)R_1$, —$S(O)_2R_1$, —$S(O)_2OR_2$, —$S(O)_2N(R_3)(R_2)$, —$C(O)R_2$, —$C(O)N(R_3)(R_2)$, —$C(O)OR_2$, —$C(O)N(R_3)(R_2)$, —$N(R_3)(R_2)$, —N(H)—N=$CH(R_1)$, —$N(R_3)C(O)R_2$, —$N(R_3)C(O)OR_2$, —$N(R_3)S(O)_2R_1$, —$N(R_3)C(O)N(R_3)(R_2)$, —$N(R_3)S(O)_2N(R_3)(R_2)$, —$R_4$, haloalkyl, cyanoalkyl, nitroalkyl, hydroxyalkyl, alkoxyalkyl, haloalkoxyalkyl, -alkylenyl-CO(O)$R_1$, -alkylenyl-OC(O)N($R_3$)($R_2$), -alkylenyl-OC(O)$OR_1$, -alkylenyl-OS(O)$_2R_1$, -alkylenyl-$SR_2$, -alkylenyl-S(O)$R_1$, -alkylenyl-S(O)$_2R_1$, -alkylenyl-S(O)$_2OR_2$, -alkylenyl-S(O)$_2N(R_3)(R_2)$, -alkylenyl-C(O)$R_2$, -alkylenyl-C(O)N($R_3$)($R_2$), -alkylenyl-C(O)$OR_2$, -alkylenyl-C(O)N($R_3$)($R_2$), -alkylenyl-N($R_3$)($R_2$), -alkylenyl-N($R_3$)C(O)$R_2$, -alkylenyl-N($R_3$)C(O)$OR_2$, -alkylenyl-N($R_3$)S(O)$_2R_1$, -alkylenyl-N($R_3$)C(O)N($R_3$)($R_2$), -alkylenyl-N($R_3$)S(O)$_2N(R_3)(R_2)$, and -alkylenyl-$R_4$;

$R_1$, at each occurrence, is independently selected from the group consisting of alkyl, alkenyl, haloalkyl, alkoxyalkyl, hlaloalkoxyalkyl, —$R_4$, and -alkylenyl-$R_4$;

$R_2$, at each occurrence, is independently selected from the group consisting of hydrogen, alkyl, alkenyl, haloalkyl, alkoxyalkyl, haloalkoxyalkyl, —$R_4$, and -alkylenyl-$R_4$;

$R_3$, at each occurrence, is independently selected from the group consisting of hydrogen, alkyl, arylalkyl, haloalkyl, and heteroarylalkyl;

$R_4$, at each occurrence, is independently selected from the group consisting of aryl, heteroaryl, heterocycle, cycloalkyl and cycloalkenyl;

$Ar_2$ is a group of formula (a), (b), (c), (d), or (e);

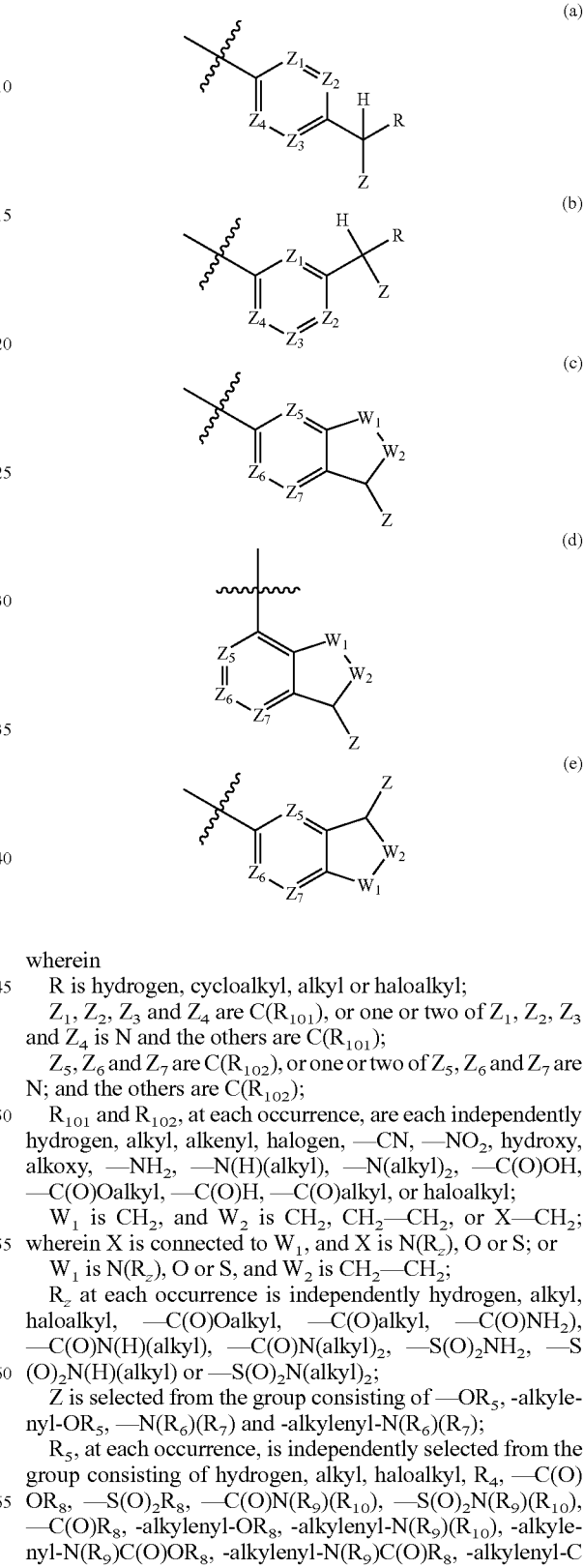

wherein

R is hydrogen, cycloalkyl, alkyl or haloalkyl;

$Z_1$, $Z_2$, $Z_3$ and $Z_4$ are $C(R_{101})$, or one or two of $Z_1$, $Z_2$, $Z_3$ and $Z_4$ is N and the others are $C(R_{101})$;

$Z_5$, $Z_6$ and $Z_7$ are $C(R_{102})$, or one or two of $Z_5$, $Z_6$ and $Z_7$ are N; and the others are $C(R_{102})$;

$R_{101}$ and $R_{102}$, at each occurrence, are each independently hydrogen, alkyl, alkenyl, halogen, —CN, —$NO_2$, hydroxy, alkoxy, —$NH_2$, —N(H)(alkyl), —N(alkyl)$_2$, —C(O)OH, —C(O)Oalkyl, —C(O)H, —C(O)alkyl, or haloalkyl;

$W_1$ is $CH_2$, and $W_2$ is $CH_2$, $CH_2$—$CH_2$, or X—$CH_2$; wherein X is connected to $W_1$, and X is N($R_z$), O or S; or $W_1$ is N($R_z$), O or S, and $W_2$ is $CH_2$—$CH_2$;

$R_z$ at each occurrence is independently hydrogen, alkyl, haloalkyl, —C(O)Oalkyl, —C(O)alkyl, —C(O)$NH_2$, —C(O)N(H)(alkyl), —C(O)N(alkyl)$_2$, —S(O)$_2NH_2$, —S(O)$_2N(H)(alkyl)$ or —S(O)$_2N(alkyl)_2$;

Z is selected from the group consisting of —$OR_5$, -alkylenyl-$OR_5$, —N($R_6$)($R_7$) and -alkylenyl-N($R_6$)($R_7$);

$R_5$, at each occurrence, is independently selected from the group consisting of hydrogen, alkyl, haloalkyl, $R_4$, —C(O)$OR_8$, —S(O)$_2R_8$, —C(O)N($R_9$)($R_{10}$), —S(O)$_2N(R_9)(R_{10})$, —C(O)$R_8$, -alkylenyl-$OR_8$, -alkylenyl-N($R_9$)($R_{10}$), -alkylenyl-N($R_9$)C(O)$OR_8$, -alkylenyl-N($R_9$)C(O)$R_8$, -alkylenyl-C (O)OR$_8$, -alkylenyl-S(O)$_2$R$_8$, -alkylenyl-S(O)$_2$N(R$_9$)(R$_{10}$), -alkylenyl-C(O)N(R$_9$)(R$_{10}$), -alkylenyl-C(O)R$_8$, and -alkylenyl-R$_4$, R$_6$, at each occurrence, is independently selected from the group consisting of hydrogen, alkyl and haloalkyl;

R$_7$, at each occurrence, is independently selected from the group consisting of hydrogen, alkyl, hydroxy, alkoxy, R$_4$, —C(=NH)NH$_2$, —C(O)OR$_8$, —S(O)$_2$R$_8$, —C(O)N(R$_9$)(R$_{11}$), —C(O)ON(R$_9$)(R$_{11}$), —S(O)$_2$N(R$_9$)(R$_{11}$), —C(O)R$_8$, —C(O)CH$_2$C(O)R$_8$, haloalkyl, -alkylenyl-OR$_8$, -alkylenyl-N(R$_9$)(R$_{11}$), -alkylenyl-N(R$_9$)C(O)OR$_8$, -alkylenyl-N(R$_9$)C(O)R$_8$, -alkylenyl-C(O)OR$_8$, -alkylenyl-S(O)$_2$R$_8$, -alkylenyl-S(O)$_2$N(R$_9$)(R$_{11}$), -alkylenyl-C(O)N(R$_9$)(R$_{11}$), -alkylenyl-C(O)R$_8$, and -alkylenyl-R$_4$, R$_8$, at each occurrence, is independently selected from the group consisting of hydrogen, alkyl, alkoxyalkyl, cyanolakyl, halaoalkyl, —R$_4$, and -alkylenyl-R$_4$;

R$_9$, at each occurrence, are each independently selected from the group consisting of hydrogen, alkyl and haloalkyl;

R$_{10}$, at each occurrence, is independently selected from the group consisting of hydrogen, alkyl, hydroxy, alkoxy, alkoxyalkyl, cyanolakyl, haloallyl, —R$_4$, and -alkylenyl-R$_4$;

R$_{11}$, at each occurrence, is independently selected from the group consisting of hydrogen, alkyl, hydroxy, alkoxy, —R$_4$, alkoxyalkyl, cyanoalkyl, haloalkyl, -alkylenyl-C(O)NH$_2$, -alkylenyl-C(O)N(H)(allyl), -alkylenyl-C(O)N(alkyl)$_2$, -alkylenyl-N(H)C(O)Oalkyl, -alkylenyl-N(alkyl)C(O)Oalkyl, and -alkylenyl-R$_4$; and the phenyl, cycloalkyl, cycloalkenyl, aryl, heteroaryl, heterocycle, aryl moiety of the arylalkyl, and the heteroaryl moiety of the heteroarylalkyl represented by Ar$_1$, R$_3$ and R$_4$, are each independently unsubstituted or substituted with 1, 2, 3 or 4 substituents independently selected from the group consisting of alkyl, alkenyl, —CN, —NO$_2$, halogen, ethylenedioxy, methylenedioxy, oxo, —OR$_a$, —OC(O)R$_a$, —OC(O)OR$_a$, —OS(O)$_2$R$_a$, —S(alkyl), —S(O)alkyl, —S(O)$_2$alkyl, —S(O)$_2$OR$_a$, —S(O)$_2$NR$_a$R$_b$, —C(O)R$_a$, —C(O)NR$_a$R$_b$, —C(O)OR$_a$, —C(O)NR$_a$R$_b$, —NR$_a$R$_b$, —NOR$_a$, —N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)R$_a$, -alkylenyl-OC(O)OR$_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)NR$_a$R$_b$, -alkylenyl-C(O)OR$_a$, -alkylenyl-C(O)NR$_a$R$_b$, -alkylenyl-NR$_a$R$_b$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$; wherein R$_a$, at each occurrence is independently selected from the group consisting of hydrogen, alkyl, alkenyl and haloalkyl, and R$_b$ at each occurrence is independently selected from the group consisting of hydrogen and alkyl.

The invention is also directed to the pharmaceutical compositions including compounds of the invention. Such compositions can be administered in accordance with a method of the invention, typically as part of a therapeutic regimen for treatment or prevention of conditions and disorders related to ACC. Another aspect of the invention relates to a method of inhibiting ACC activity. The method is useful for treating, or preventing conditions and disorders related to ACC in mammals. More particularly, the method is useful for treating or preventing conditions and disorders related to metabolic syndrome, type II diabetes, obesity, atherosclerosis and cardiovascular diseases in mammals. Accordingly, the compounds and compositions of the invention are useful as a medicament for treating or preventing disease modulated by ACC.

Processes for making compounds of the invention also are contemplated. The compounds, compositions including the compounds, methods for making the compounds, and methods for treating or preventing conditions and disorders by administering the compounds are further described herein.

DETAILED DESCRIPTION OF THE INVENTION

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture.

Certain terms as used in the specification are intended to refer to the following definitions, as detailed below.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkoxyalkyl" as used herein, means an alkyl group, as defined herein, in which one or two hydrogen atoms are replaced by alkoxy groups, as defined herein. Representative examples of alkoxyalkyl include, but are not limited to, methoxymethyl and ethoxymethyl.

The term "alkyl" as used herein, means a straight or branched chain hydrocarbon containing from 1 to 10 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n heptyl, n-octyl, n-nonyl, and n-decyl.

The term "alkylenyl" as used herein, means a divalent group derived from a straight or branched chain hydrocarbon of from 1 to 6 carbon atoms. Representative examples of alkylenyl include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, dihydroindenyl, indenyl, naphthyl, dihydronaphthalenyl, and 5,6,7,8-tetrahydronaphthalenyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "cyano" as used herein, means —CN.

The term "cyanoalkyl" as used herein, means an alkyl group as defined herein, in which one or two hydrogen atoms are replaced by cyano. Representative examples of cyanoalkyl include, but are not limited to, 1-methyl-1-cyanoethyl and cyanoethyl.

The term "cycloalkyl" or "cycloalkane" as used herein, means a monocyclic or bicyclic cycloalkyl. The monocyclic cycloalkyl has three to eight carbon atoms, zero heteroatom and zero double bond. The monocyclic cycloalkyl can be attached to the parent molecular moiety through any substitutable atom contained within the monocyclic cycloalkyl Examples of monocyclic cycloalkyls include, but are not limited to, cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl. The bicyclic cycloalkyl can be attached to the parent molecular moiety through any substitutable atom contained within the bicyclic cycloalkyl. The monocyclic and bicyclic cycloalkyl groups of the present invention can be unsubstituted or substituted.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatom. The four-membered ring systems have one double bond, the five- or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The bicyclic cycloalkenyl can be attached to the parent molecular moiety through any substitutable atom contained within the bicyclic cycloalkenyl. Representative examples of the bicyclic cycloalkenyl groups include, but not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "ethylenedioxy" as used herein, means a —O—$(CH_2)_2$—O— group wherein the oxygen atoms of the ethylenedioxy group are attached to two adjacent carbon atoms of the parent molecular moiety, forming a six membered ring with the parent molecular moiety.

The term "halo" or "halogen" as used herein, means —Cl, —Br, —I or —F.

The term "haloalkoxy" as used herein, means an alkoxy group, as defined herein, in which one, two, three or four hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkoxyalkyl" as used herein, means a haloalkoxy group, as defined herein, appended to the parent moiety through an alkyl group, as defined herein.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, difluoromethyl, trifluoromethyl, pentafluoroethyl, and 2-chloro-3-fluoropentyl.

The term "heterocycle" or "heterocyclic" as used herein, means a monocyclic heterocycle or a bicyclic heterocycle. The monocyclic heterocycle is a three-, foul-, five-, six- or seven-membered ring containing at least one heteroatom independently selected from the group consisting of O, N, and S. The three- or four membered ring contains zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two, or three double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodithiolyl, benzopyranyl, benzothiopyranyl, 2,3-dihydrobenzofuranyl, 2,3-dihydrobenzothienyl, 2,3-dihydro-1H-indolyl, 2,3-dihydroisoindol-2-yl, 2,3-dihydroisoindol-3-yl, 1,3-dioxo-1H-isoindolyl, 2-(trifluoromethyl)-5,6-dihydroimidazo-[1,2-a]pyrazin-7(8H)-yl, 1-acetyl-2,3-dihydro-1H-indol-6-yl, 3-(trifluoromethyl)-5,6-dihydro[1,2,4]triazolo[4,3-a]pyrazin-7(8H)-yl, 1,2,3,4-tetrahydroisoquinolin-2-yl, and 1,2,3,4-tetrahydroquinolinyl. The monocyclic and bicyclic heterocycle of the present invention can be unsubstituted or substituted.

The term "heteroaryl" as used herein, means a monocyclic heteroaryl or a bicyclic heteroaryl. The monocyclic heteroaryl is a five- or six-membered ring. The monocyclic five-membered heteroaryls have two double bonds and the monocyclic six-membered heteroaryls have three double bonds. The monocyclic heteroaryl has at least one carbon atom in the ring replaced by heteroatoms selected from sulfur, nitrogen and oxygen. For example, the monocyclic five-membered heteroaryl can contain one sulfur, nitrogen or oxygen atom, and the others are carbon. Alternatively, the five-membered heteroaryl can have four nitrogen atoms. The five-membered heteroaryl can also have one or two nitrogen atoms and an additional heteroatom selected from nitrogen, oxygen and sulfur atom. The six-membered monocyclic heteroaryls can have up to three carbon atoms in the ring replaced by nitrogen atoms. The monocyclic heteroaryl is corrected to the parent molecular moiety through any substitutable atom contained within the monocyclic heteroaryl, Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl groups include, but not limited to, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, and 5,6,7,8-tetrahydroquinolin-5-yl. The monocyclic and bicyclic heteroaryl groups of the present invention can be substituted or unsubstituted.

The term "heteroarylalkyl" as used herein, refers to a heteroaryl group, as defined herein, appended to the parent molecular moiety through an alkyl group, as defined herein. Representative examples of heteroarylalkyl include, but not limited to, pyridinylmethyl, thienylethyl, thiadiazolylmethyl.

The term "heteroatom" as used herein, refers to nitrogen, oxygen or sulfur atom.

The term "hydroxy" or "hydroxyl" as used herein, means an —OH group.

The term "hydroxyalkyl" as used herein, means an alkyl group, as defined herein, in which one or two hydrogen atoms are replaced by a hydroxyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "methylenedioxy" as used herein, means a —O—($CH_2$)—O— group wherein the oxygen atoms of the methylenedioxy group are attached to two adjacent carbon atoms of the parent molecular moiety, forming a five membered ring with the parent molecular moiety.

The term "nitro" as used herein, refers to an —$NO_2$ group.

The term "nitroalkyl" as used herein, means a nitro group, as defined herein, appended to the parent moiety through an alkyl group, as defined herein.

The term "oxo" as used herein, means =O.

Compounds of the invention can have the formula (I) as described above.

In compounds of formula (I), $Ar_1$ is selected from the group consisting of phenyl and a monocyclic, five or six-membered heteroaryl; each of which is independently unsubstituted or substituted as described in formula (I). Particularly, $Ar_1$ is phenyl, pyridinyl, thienyl, furanyl, thiazolyl, oxazolyl, isoxazolyl, 1,3,4-thiadiazolyl, 1,2,4-thiadiazolyl, or 1,2,4-oxadiazolyl, each of which is independently unsubstituted or substituted as described in formula (I). More particularly, $Ar_1$ is phenyl, pyridinyl, thienyl, furanyl, 1,3-thiazolyl, or 1,3,4-thiadiazolyl, each of which is independently unsubstituted or substituted with one substituent selected from the group consisting of —I, —Br, —Cl, and —F. Preferably, $Ar_1$ is thiazolyl, unsubstituted or, substituted with one substituent selected from the group consisting of —I, —Br, —Cl, and —F.

$Ar_2$ is a group of formula (a), (b), (c), (d), or (e)

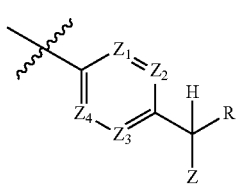

(a)

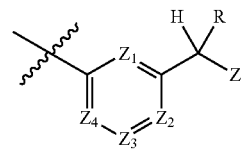

(b)

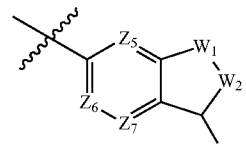

(c)

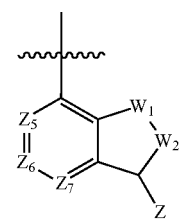

(d)

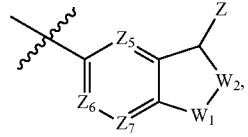

(e)

wherein $Z_1$, $Z_2$, $Z_3$, $Z_4$, $Z_5$, $Z_6$, $Z_7$, $W_1$, $W_2$, R and Z are as defined in formula (I). Particularly, $Ar_2$ is a group of formula (a), (b) or (c), wherein R is hydrogen, cycloalkyl, alkyl or haloalkyl, Particularly, R is $C_1$-$C_6$ alkyl or haloalkyl. More particularly, R is methyl or trifluoromethyl.

$Z_1$, $Z_2$, $Z_3$ and $Z_4$ are C($R_{101}$), or one or two of $Z_1$, $Z_2$, $Z_3$ and $Z_4$ is N and the others are C($R_{101}$); wherein $R_{101}$ is as defined in formula (I), Particularly, $Z_1$, $Z_2$, $Z_3$ and $Z_4$ are C($R_{101}$) or one of $Z_1$, $Z_2$, $Z_3$ and $Z_4$ is N; and the others are C($R_{101}$) wherein $R_{101}$ is as defined in formula (I). More particularly, $Z_1$, $Z_2$, $Z_3$ and $Z_4$ are C($R_{101}$), or one of $Z_1$, $Z_2$, $Z_3$ and $Z_4$ is N; and the others are C($R_{101}$) and $R_{101}$ is hydrogen or $C_1$-$C_6$ alkyl. More particularly, $R_{101}$ is hydrogen.

$Z_5$, $Z_6$ and $Z_7$ are C($R_{102}$), or one or two of $Z_5$, $Z_6$ and $Z_7$ are N and the others are C($R_{102}$) wherein $R_{102}$ is as defined in formula (I), Particularly, $Z_5$, $Z_6$ and $Z_7$ are C($R_{102}$) wherein $R_{102}$ is hydrogen or $C_1$-$C_6$ alkyl. More particularly, $Z_5$, $Z_6$ and $Z_7$ are C($R_{102}$) wherein $R_{102}$ is hydrogen.

$W_1$ is $CH_2$, and $W_2$ is $CH_2$, $CH_2$—$CH_2$, or X—$CH_2$; wherein X is connected to $W_1$ and X is N($R_z$), O or S; or $W_1$ is N($R_z$), O or S, and $W_2$ is $CH_2$—$CH_2$; and $R_z$ is as defined in formula (I). Particularly, $W_1$ and $W_2$ are each $CH_2$.

Z is selected from the group consisting of —$OR_5$, -alkylenyl-$OR_5$, —N($R_6$)($R_7$) and -alkylenyl-N($R_6$)($R_7$) wherein $R_5$, $R_6$ and $R_7$ are as described in formula (I). Particularly, Z is selected from the group consisting of —$OR_5$ and —N($R_6$)($R_7$) wherein $R_5$, $R_6$ and $R_7$ are as described in formula (I). More particularly, Z is —N($R_6$)($R_7$) wherein $R_6$ and $R_7$ are as described in formula (I). Even more particularly, Z is —N($R_6$)($R_7$) wherein $R_6$ is hydrogen, and $R_7$ is selected from the group consisting of —C(O)$R_8$, —C(O)$OR_8$ and —C(O)N($R_9$)($R_{11}$) wherein $R_8$ is $C_1$-$C_6$ alkyl, $R_9$ is hydrogen and $R_{11}$ is hydrogen or $C_1$-$C_6$ alkyl. Preferably, Z is —N($R_6$)($R_7$) wherein $R_6$ is hydrogen, and $R_7$ is selected from the group consisting of —C(O)R$_8$, —C(O)OR$_8$ and —C(O)N(R$_9$)(R$_{11}$) wherein R$_8$ is methyl, R$_9$ is hydrogen and R$_{11}$ is hydrogen or methyl.

Ar$_3$ is phenyl or monocyclic heteroaryl; each of which is independently unsubstituted or substituted as described in formula (I). Particularly, Ar$_3$ is selected from the group of formula

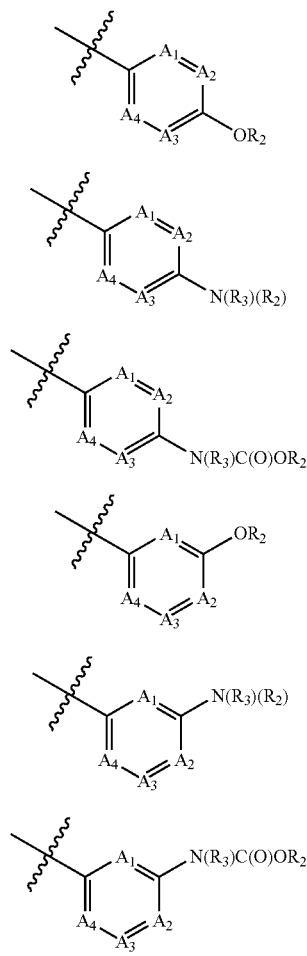

A$_1$, A$_2$, A$_3$ and A$_4$ are —C(R$_v$)—, or one or two of A$_1$, A$_2$, A$_3$ and A$_4$ is N and the others are —C(R$_v$)—, wherein R$_v$ is selected from the group consisting of hydrogen, alkyl, alkenyl, CN, NO$_2$, halogen, hydroxy, alkoxy, —NH$_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl; and R$_2$ and R$_3$ are as defined in formula (I). More particularly, Ar$_3$ is of formula (f), (g), (h), (i), (j) or (k); wherein A$_1$, A$_2$, A$_3$ and A$_4$ are —C(R$_v$)—; or one of A$_1$, A$_2$, A$_3$ and A$_4$ are N and the others are —C(R$_v$)—; wherein R$_v$ is as described above. Preferably, Ar$_3$ is of formula (f), (g), (h), (i), (j) or (k), wherein A$_1$, A$_2$, A$_3$ and A$_4$ are —C(R$_v$)—; or one of A$_1$, A$_2$, A$_3$ and A$_4$ are N and the others are —C(R$_v$)—; wherein R$_v$ is selected from the group consisting of hydrogen, —I, —Br, —Cl, and —F, R$_3$ is hydrogen and R$_2$ at each occurrence is independently selected from the group consisting of alkyl, —R$_4$ and -alkylenyl-R$_4$ wherein R$_4$ is selected from the group consisting of cycloalkyl, heterocycle and aryl, each of which is independently unsubstituted or substituted as described in formula (I). More preferably, Ar$_3$ is of formula (f) wherein A$_1$, A$_2$, A$_3$ and A$_4$ are —C(R$_v$)—; or one of A$_1$, A$_2$, A$_3$ and A$_4$ are N and the others are —C(R$_v$)—, wherein R$_v$ is selected from the group consisting of hydrogen, —I, —Br, —Cl and —F; and R$_2$ is C$_1$-C$_6$ alkyl. Even more preferably, Ar$_3$ is of formula (f) wherein A$_1$, A$_2$, A$_3$ and A$_4$ are —C(R$_v$)—; wherein R$_v$ is selected from the group consisting of hydrogen, —I, —Br, —Cl and —F; and R$_2$ is selected from the group consisting of methyl, ethyl, isopropyl and 2-methylpropyl, Y is selected from the group consisting of —(CR$_x$R$_y$)—, —C(O)—, —O—, —N(H)—, —N(alkyl)- and —S— wherein R$_x$ and R$_y$, are as described in formula (I). Particularly, Y is —CH$_2$—, —C(O)—, —O—, —N(H)—, —N(alkyl)- or —S—Preferably, Y is —O—.

It is appreciated that the present invention contemplates compounds of formula (I) with combinations of the above embodiments, including particular, more particular, preferred, more preferred and most preferred embodiments.

Accordingly, one aspect of the invention is related to compounds of formula (I) wherein Ar$_3$ is

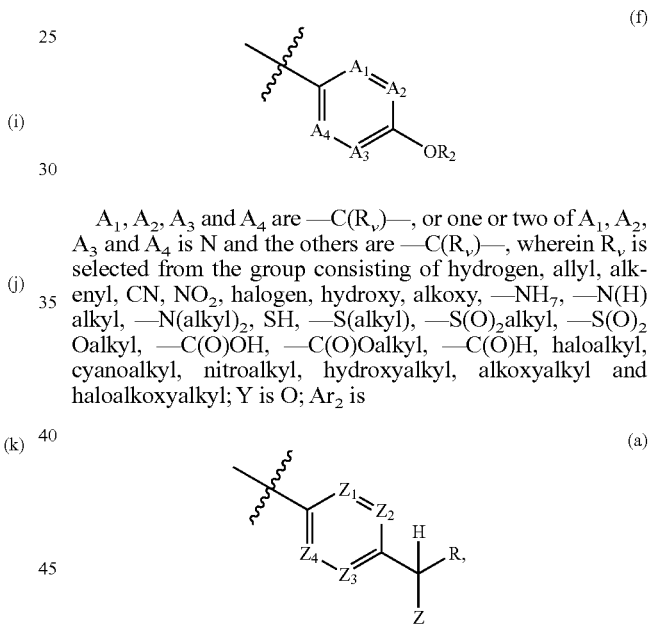

A$_1$, A$_2$, A$_3$ and A$_4$ are —C(R$_v$)—, or one or two of A$_1$, A$_2$, A$_3$ and A$_4$ is N and the others are —C(R$_v$)—, wherein R$_v$ is selected from the group consisting of hydrogen, allyl, alkenyl, CN, NO$_2$, halogen, hydroxy, alkoxy, —NH$_7$, —N(H)alkyl, —N(alkyl)$_2$, SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl; Y is O; Ar$_2$ is

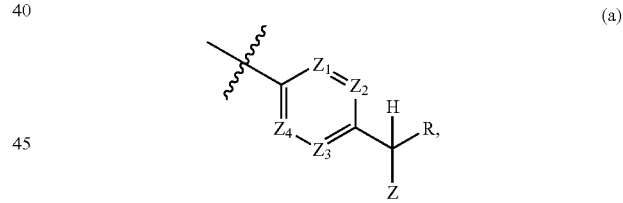

and R$_2$, Ar$_1$, Z$_1$, Z$_2$, Z$_3$, Z$_4$, R and Z are as defined in formula (I). Preferably, A$_1$, A$_2$, A$_3$ and A$_4$ are —C(R$_v$)—, or one of A$_1$, A$_2$, A$_3$ and A$_4$ is N and the others are C(R$_v$)—; wherein R$_v$ is selected from the group consisting of hydrogen, —I, —Br, —Cl and —F; Y is —O—; Ar$_2$ is

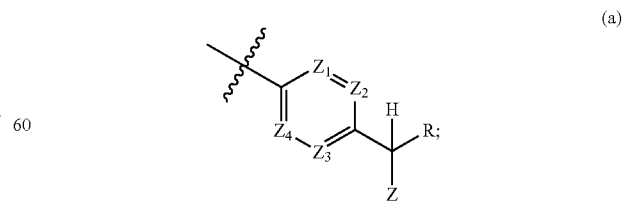

wherein Z$_1$, Z$_2$, Z$_3$, Z$_4$ are C(R$_{101}$), or one of Z$_1$, Z$_2$, Z$_3$, Z$_4$ is N and the others are C(R$_{101}$); R$_{101}$ is hydrogen or C$_1$-C$_6$ alkyl; and R$_2$, Ar$_1$, R and Z are as defined in formula (I). More preferably, $A_1$, $A_2$, $A_3$ and $A_4$ are —C($R_\nu$)— wherein $R_\nu$ is selected from the group consisting of hydrogen, —I, —Br, —Cl and —F; Y is —O—; $Ar_2$ is formula (a) wherein $Z_1$, $Z_2$, $Z_3$, $Z_4$ are C($R_{101}$), or one of $Z_1$, $Z_2$, $Z_3$, $Z_4$ is N and the others are C($R_{101}$); $R_{101}$ is hydrogen; and $R_2$, $Ar_1$, R and Z are as defined in formula (I).

Another aspect of the invention relates to compounds of formula (I), or a pharmaceutically acceptable salt, prodrug, salt of a prodrug, or a combination thereof, wherein $Ar_3$ is

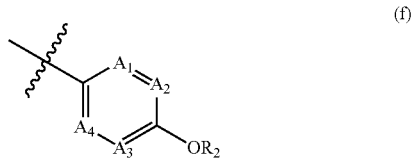

(f)

$A_1$, $A_2$, $A_3$ and $A_4$ are —C($R_\nu$)—, or one of $A_1$, $A_2$, $A_3$ and $A_4$ is N and the others are —C($R_\nu$)—, wherein $R_\nu$ is selected from the group consisting of hydrogen, alkyl, alkenyl, CN, $NO_2$, halogen, hydroxy, alkoxy, —$NH_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl; $R_2$ is alkyl; $Ar_1$ is selected from the group consisting of phenyl and a monocyclic, five or six-membered heteroaryl; each of which is independently unsubstituted or substituted as described in formula (I); Y is O; $Ar_2$ is

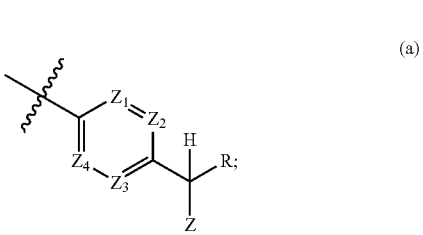

(a)

$Z_1$, $Z_2$, $Z_3$ and $Z_4$ are C($R_{101}$), or one of $Z_1$, $Z_2$, $Z_3$ and $Z_4$ is N and the others are C($R_{101}$); wherein $R_{101}$ is as defined in formula (I); R is alkyl or haloalkyl; and Z is N($R_6$)($R_7$); wherein $R_6$ is hydrogen or alkyl, and $R_7$ is selected from the group consisting of —C(O)Oalkyl, —C(O)$NH_2$, —C(O)N(H)(alkyl) and —C(O)alkyl. Particularly, the invention is directed to compounds of formula (I), wherein $Ar_3$ is formula (f), wherein $A_1$, $A_2$, $A_3$ and $A_4$ are —C($R_\nu$)—, or one of $A_1$, $A_2$, $A_3$ and $A_4$ is N and the others are —C($R_\nu$)—, wherein $R_\nu$ is selected from the group consisting of hydrogen, —I, —Br, —Cl, and —F; $R_2$ is $C_1$-$C_6$ alkyl; $Ar_1$ is selected from the group consisting of phenyl, pyridinyl, thienyl, furanyl, thiazolyl, oxazolyl, isoxazolyl, 1,3,4-thiadiazolyl, 1,2,4-thiadiazoyl), and 1,2,4-oxadiazolyl, each of which is independently unsubstituted or substituted with one substituent selected from the group consisting of —I, —Br, —Cl, and —F; Y is O; $Ar_2$ is formula (a) wherein $Z_1$, $Z_2$, $Z_3$ and $Z_4$ are C($R_{101}$), or one of $Z_1$, $Z_2$, $Z_3$ and $Z_4$ is N and the others are C($R_{101}$); $R_{101}$ is selected from the group consisting of hydrogen and $C_1$-$C_6$ alkyl; R is $C_1$-$C_6$ alkyl or haloalkyl; and Z is N($R_6$)($R_7$); wherein $R_6$ is hydrogen or $C_1$-$C_6$ alkyl, and $R_7$ is selected from the group consisting of —C(O)O($C_1$-$C_6$ alkyl), —C(O)$NH_7$, —C(O)N(H)($C_1$-$C_6$ alkyl) and —C(O)($C_1$-$C_6$ alkyl). More particularly, the invention is related to compounds of formula (I) wherein $Ar_3$ is formula (f) wherein $A_1$, $A_2$, $A_3$ and $A_4$ are —C($R_\nu$)—, and $R_\nu$ is selected from the group consisting of hydrogen, —I, —Br, —Cl, and —F; $R_2$ is $C_1$-$C_6$ alkyl; $Ar_1$ is thiazolyl, unsubstituted or substituted with one substituent selected from the group consisting of —I, —Br, —Cl, and —F; Y is O; $Ar_2$ is formula (a) wherein $Z_1$, $Z_2$, $Z_3$ and $Z_4$ are C($R_{101}$), or one of $Z_1$, $Z_2$, $Z_3$ and $Z_4$ is N and the others are C($R_{101}$); $R_{101}$ is hydrogen; R is $C_1$-$C_6$ alkyl; and Z is N($R_6$)($R_7$); wherein $R_6$ is hydrogen; and $R_7$ is selected from the group consisting of —C(O)O($C_1$-$C_6$ alkyl), —C(O)$NH_2$, —C(O)N(H)($C_1$-$C_6$ alkyl) and —C(O)($C_1$-$C_6$ alkyl).

Another aspect of the invention relates to compound of claim 2 having formula (I), or a pharmaceutically acceptable salt, prodrug, salt of a prodrug, or combination thereof wherein $Ar_3$ is

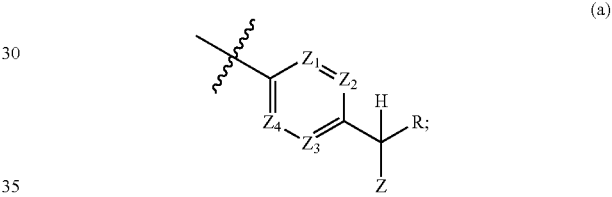

(f)

$A_1$, $A_2$, $A_3$ and $A_4$ are —C($R_\nu$)—, wherein $R_\nu$ is selected from the group consisting of hydrogen, —I, —Br, —Cl, and —F; $R_2$ is selected from the group consisting of methyl, ethyl, isopropyl, and 2-methylpropyl; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; Y is O; $Ar_2$ is

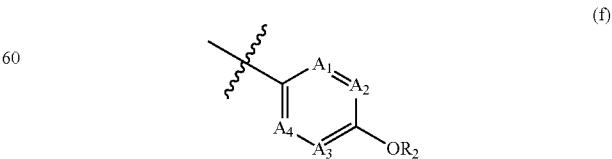

(a)

$Z_1$, $Z_2$, $Z_3$ and $Z_4$ are C($R_{101}$), or one of $Z_1$, $Z_2$, $Z_3$ and $Z_4$ is N and the others are C($R_{101}$); wherein $R_{101}$ is hydrogen, methyl or ethyl; R is methyl or trifluoromethyl; and Z is N($R_6$)($R_7$); wherein $R_6$ is hydrogen or methyl, and $R_7$ is selected from the group consisting of —C(O)O-methyl, —C(O)$NH_2$, —C(O)N(H)(methyl); and —C(O)methyl. Particularly, the invention directs to compounds of formula (I) wherein $Ar_3$ is formula (f) wherein $A_1$, $A_2$, $A_3$ and $A_4$ are —C($R_\nu$)—, wherein $R_\nu$ is selected from the group consisting of hydrogen, —I, —Br, —Cl, and —F; $R_2$ is selected from the group consisting of methyl and isopropyl; $Ar_1$ is thiazolyl; unsubstituted or substituted with one substituent selected from the group consisting of —I, —Br, —Cl, and —F; Y is O; $Ar_2$ is formula (a) wherein $Z_1$, $Z_2$, $Z_3$ and $Z_4$ are C($R_{101}$), or one of $Z_1$, $Z_2$, $Z_3$ and $Z_4$ is N and the others are C($R_{101}$); wherein $R_{101}$ is hydrogen; R is methyl; and Z is N($R_6$)($R_7$); wherein $R_6$ is hydrogen, and $R_7$ is selected from the group consisting of —C(O)O-methyl, —C(O)$NH_2$, —C(O)N(H)(methyl); and —C(O)methyl.

Another aspect of the invention relates to compounds of formula (I), or a pharmaceutically acceptable salt, prodrug, salt of a prodrug, or a combination thereof wherein $Ar_3$ is wherein $A_1$, $A_2$, $A_3$ and $A_4$ are —C($R_\nu$)—, or one or two of $A_1$, $A_2$, $A_3$ and $A_4$ are N and the others are —C($R_\nu$)—, wherein $R_\nu$ is selected from the group consisting of hydrogen, alkyl, alkenyl, CN, $NO_2$, halogen, hydroxy, alkoxy, —$NH_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl; Y is O; and $Ar_2$ is

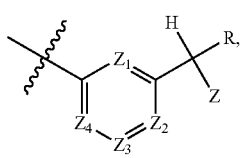

(b)

and $R_2$, $Ar_1$, $Z_1$, $Z_2$, $Z_3$, $Z_4$, R and Z are as defined in formula (I). Preferably, $A_1$, $A_2$, $A_3$ and $A_4$ are —$C(R_v)$—, or one of $A_1$, $A_2$, $A_3$ and $A_4$ is N and the others are —$C(R_v)$—; wherein $R_v$ is selected from the group consisting of hydrogen, —I, —Br, —Cl and —F; Y is —O—; $Ar_2$ is formula (b) wherein $Z_1$, $Z_2$, $Z_3$, $Z_4$ are $C(R_{101})$, or one of $Z_1$, $Z_2$, $Z_3$, $Z_4$ is N and the others are $C(R_{101})$; $R_{101}$ is hydrogen or $C_1$-$C_6$ alkyl; and $R_2$, $Ar_1$, R and Z are as defined in formula (I). More preferably, $A_1$, $A_2$, $A_3$ and $A_4$ are —$C(R_v)$—, wherein $R_v$ is selected from the group consisting of hydrogen, —I, —Br, —Cl and —F; Y is —O—; Ar) is formula (b) wherein $Z_1$, $Z_2$, $Z_3$, $Z_4$ are $C(R_{101})$, or one of $Z_1$, $Z_2$, $Z_3$, $Z_4$ is N and the others are $C(R_{101})$; $R_{101}$ is hydrogen; and $R_2$, $Ar_1$, R and Z are as defined in formula (I).

Another aspect of the invention relates to compounds of formula (I), or a pharmaceutically acceptable salt, prodrug, salt of a prodrug, or a combination thereof, wherein $Ar_3$ is

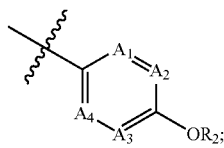

(f)

wherein $A_1$, $A_2$, $A_3$ and $A_4$ are —$C(R_v)$—, or one of $A_1$, $A_2$, $A_3$ and $A_4$ is N and the others are —$C(R_v)$— and $R_v$ is as defined above; $R_2$ is alkyl; $Ar_1$ is selected from the group consisting of phenyl and a monocyclic, five or six-membered heteroaryl; each of which is independently unsubstituted or substituted as described in formula (I); Y is O; $Ar_2$ is

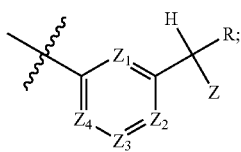

(b)

wherein $Z_1$, $Z_2$, $Z_3$ and $Z_4$ are $C(R_{101})$, or one of $Z_1$, $Z_2$, $Z_3$ and $Z_4$ is N and the others are $C(R_{101})$; $R_{101}$ is as defined in formula (I); R is alkyl or haloalkyl; and Z is $N(R_6)(R_7)$; wherein $R_6$ is hydrogen or alkyl, and $R_7$ is selected from the group consisting of —C(O)Oalkyl, —C(O)$NH_2$, —C(O)N(H)(alkyl) and —C(O)alkyl. Particularly, the invention is directed to compounds of formula (I), wherein $Ar_3$ is formula (f), wherein $A_1$, $A_2$, $A_3$ and $A_4$ are —$C(R_v)$—, or one of $A_1$, $A_2$, $A_3$ and $A_4$ is N and the others are —$C(R_v)$—, wherein $R_v$ is selected from the group consisting of hydrogen, —I, —Br, —Cl, and —F; $R_2$ is $C_1$-$C_6$ alkyl; $Ar_1$ is selected from the group consisting of phenyl, pyridinyl, thienyl, furanyl, thiazolyl, oxazolyl, isoxazolyl, 1,3,4-thiadiazolyl, 1,2,4-thiadiazolyl, and 1,2,4-oxadiazolyl, each of which is independently unsubstituted or substituted with one substituent selected from the group consisting of —I, —Br, —Cl, and —F; Y is O; $Ar_2$ is formula (b) wherein $Z_1$, $Z_7$, $Z_3$ and $Z_4$ are $C(R_{101})$, or one of $Z_1$, $Z_2$, $Z_3$ and $Z_4$ is N and the others are $C(R_{101})$; $R_{101}$ is selected from the group consisting of hydrogen and $C_1$-$C_6$ alkyl; R is $C_1$-$C_6$ alkyl or haloalkyl; and Z is $N(R_6)(R_7)$; wherein $R_6$ is hydrogen or $C_1$-$C_6$ alkyl, and $R_7$ is selected from the group consisting of —C(O)O($C_1$-$C_6$ alkyl), —C(O)$NH_2$, —C(O)N(H)($C_1$-$C_6$ alkyl) and —C(O)($C_1$-$C_6$ alkyl). More particularly, the invention is directed to compounds of formula (I), wherein $Ar_3$ is formula (f), wherein $A_1$, $A_2$, $A_3$ and $A_4$ are —$C(R_v)$— wherein $R_v$ is selected from the group consisting of hydrogen, —I, —Br, —Cl, and —F; $R_2$ is $C_1$-$C_6$ alkyl; $Ar_1$ is thiazolyl, unsubstituted or substituted with one substituent selected from the group consisting of —I, —Br, —Cl, and —F; Y is O; $Ar_2$ is formula (b) wherein $Z_1$, $Z_2$, $Z_3$ and $Z_4$ are $C(R_{101})$, or one of $Z_1$, $Z_2$, $Z_3$ and $Z_4$ is N and the others are $C(R_{101})$; $R_{101}$ is hydrogen; R is $C_1$-$C_6$ alkyl or haloalkyl; and Z is $N(R_6)(R_7)$; wherein $R_6$ is hydrogen, and $R_7$ is selected from the group consisting of —C(O)O($C_1$-$C_6$ alkyl), —C(O)$NH_2$, —C(O)N(H)($C_1$-$C_6$ alkyl) and —C(O)($C_1$-$C_6$ alkyl).

Another aspect of the invention relates to compound of formula (I), or a pharmaceutically acceptable salt, prodrug, salt of a prodrug, or a combination thereof wherein $Ar_3$ is

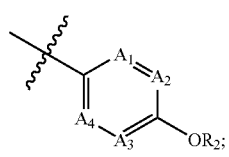

(f)

$A_1$, $A_2$, $A_3$ and $A_4$ are —$C(R_v)$—, wherein $R_v$ is selected from the group consisting of hydrogen, —I, —Br, —Cl, and —F; $R_2$ is selected from the group consisting of methyl, ethyl, isopropyl, and 2-methylpropyl; $Ar_1$ is selected from the group consisting of phenyl, pyridinyl, thienyl, furanyl, thiazolyl, and 1,3,4-thiadiazolyl; each of which is independently unsubstituted or substituted with one substituent selected from the group consisting of —I, —Br, —Cl, and —F; Y is O; $Ar_2$ is formula (b) wherein $Z_1$, $Z_2$, $Z_3$ and $Z_4$ are $C(R_{101})$, or one of $Z_1$, $Z_2$, $Z_3$ and $Z_4$ is N and the others are $C(R_{101})$; wherein $R_{101}$ is hydrogen, methyl or ethyl; R is methyl or tuifluoromethyl; and Z is $N(R_6)(R_7)$; wherein $R_6$ is hydrogen or methyl, and $R_7$ is selected from the group consisting of —C(O)O-methyl, —C(O)$NH_2$, —C(O)N(H)(methyl); and —C(O)methyl, Particularly, the invention directs to compounds of formula (I) wherein $Ar_3$ is formula (f) wherein $A_1$, $A_2$, $A_3$ and $A_4$ are —$C(R_v)$—, wherein $R_v$ is selected from the group consisting of hydrogen, —I, —Br, —Cl, and —F; $R_2$ is selected from the group consisting of methyl and isopropyl; $Ar_1$ is thiazolyl; unsubstituted or substituted with one substituent selected from the group consisting of —I, —Br, —Cl, and —F; Y is O; $Ar_2$ is formula (b) wherein $Z_1$, $Z_2$, $Z_3$ and $Z_4$ are $C(R_{101})$, or one of $Z_1$, $Z_2$, $Z_3$ and $Z_4$ is N and the others are $C(R_{101})$; wherein $R_{101}$ is hydrogen; R is methyl; and Z is $N(R_6)(R_7)$; wherein $R_6$ is hydrogen, and $R_7$ is selected from the group consisting of —C(O)O-methyl, —C(O)$NH_2$, —C(O)N(H)(methyl); and —C(O)methyl.

Another aspect of the invention relates to compounds of formula (I), or a pharmaceutically acceptable salt, prodrug, salt of a prod-g, or a combination thereof, wherein $Ar_3$ is

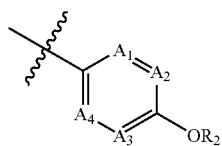
(f)

$A_1$, $A_2$, $A_3$ and $A_4$ are —C($R_v$)—, or one or two of $A_1$, $A_2$, $A_3$ and $A_4$ is N and the others are —C($R_v$)—, wherein $R_v$ is selected from the group consisting of hydrogen, alkyl, alkenyl, CN, $NO_2$, halogen, hydroxy, alkoxy, —$NH_2$, —N(H)alkyl, —N(alkyl)$_2$, —SH, —S(alkyl), —S(O)$_2$allyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl; Y is O; $Ar_2$ is a group of formula (c), (d) or (e)

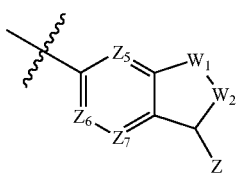
(c)

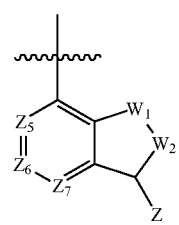
(d)

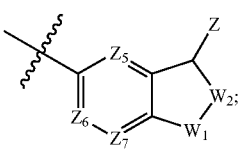
(e)

and $R_2$, $Ar_1$, $Z_5$, $Z_6$, $Z_6$, $W_1$, $W_2$ and Z are as defined in formula (I). Particularly, $A_1$, $A_2$, $A_3$ and $A_4$ are —C($R_v$)—, or one of $A_1$, $A_2$, $A_3$ and $A_4$ is N and the others are —C($R_v$)—, wherein $R_v$ is selected from the group consisting of hydrogen, —I, —Br, —Cl, and —F; Y is —O—; $Ar_2$ is formula (c), (d) or (e) wherein $Z_5$, $Z_6$, $Z_6$ are C($R_{102}$); $R_{102}$ is hydrogen; $W_1$ and $W_2$ are each —$CH_2$—; and $R_2$, $Ar_1$ and Z are as defined in formula (I). More particularly, $A_1$, $A_7$, $A_3$ and $A_4$ are —C($R_v$)— wherein $R_v$ is selected from the group consisting of hydrogen, —I, —Br, —Cl, and —F; Y is —O—; $Ar_2$ is formula (c), (d) or (e) wherein $Z_5$, $Z_6$, $Z_6$ are C($R_{102}$); $R_{102}$ is hydrogen; $W_1$ and $W_2$ are each —$CH_2$—; and $R_2$, $Ar_1$ and Z are as defined in formula (I). Another aspect of the invention relates to compounds of formula (I), or a pharmaceutically acceptable salt, prodrug, salt of a prodrug, or a combination thereof, wherein $Ar_3$ is

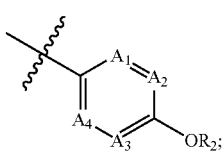
(f)

$A_1$, $A_2$, $A_3$ and $A_4$ are —C($R_v$)—, or one $A_1$, $A_2$, $A_3$ and $A_4$ is N and the others are —C($R_v$)—; wherein $R_v$ is as defined above; $R_2$ is alkyl; $Ar_1$ is selected from the group consisting of phenyl and a monocyclic, five or six-membered heteroaryl; each of which is independently unsubstituted or substituted as described in formula (I); Y is O; $Ar_2$ is

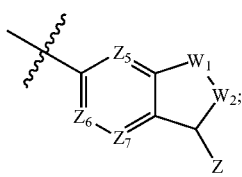
(c)

$Z_5$, $Z_6$ and $Z_7$ are C($R_{102}$); $R_{102}$ is as defined in formula (I); $W_1$ is $CH_2$; $W_2$ is $CH_2$; and Z is N($R_6$)($R_7$); wherein $R_6$ is hydrogen or alkyl, and $R_7$ is selected from the group consisting of —C(O)Oalkyl, —C(O)$NH_2$, —C(O)N(H)(alkyl) and —C(O)alkyl Particularly, the invention is directed to compounds of formula (I), wherein $Ar_3$ is of formula (f) wherein $A_1$, $A_2$, $A_3$ and $A_4$ are —C($R_v$)—, or one $A_1$, $A_2$, $A_3$ and $A_4$ is N and the others are —C($R_v$)—; $R_v$ is selected from the group consisting of hydrogen, —I, —Br, —Cl and —F; $R_2$ is $C_1$-$C_6$ alkyl; $Ar_1$ is selected from the group consisting of phenyl, pyridinyl, thienyl, furanyl, thiazolyl, oxazolyl, isoxazolyl, 1,3,4-thiadiazolyl, 1,2,4-thiadiazolyl, and 1,2,4-oxadiazolyl, each of which is independently unsubstituted or substituted with one substituent selected from the group consisting of —I, —Br, —Cl, and —F; Y is O; $Ar_2$ is formula (c) wherein $Z_5$, $Z_6$ and $Z_7$ are C($R_{102}$); $R_{102}$ is hydrogen or $C_1$-$C_6$ alkyl; $W_1$ and $W_2$ are each —$CH_2$—; and Z is N($R_6$)($R_7$); wherein $R_6$ is hydrogen or $C_1$-$C_6$ alkyl, and $R_7$ is selected from the group consisting of —C(O)O($C_1$-$C_6$ alkyl), —C(O)$NH_2$, —C(O)N(H)($C_1$-$C_6$ alkyl) and —C(O)($C_1$-$C_6$ alkyl). More particularly, the invention is directed to compounds of formula (I), wherein $Ar_3$ is of formula (f) wherein $A_1$, $A_2$, $A_3$ and $A_4$ are —C($R_v$)— and $R_v$ is selected from the group consisting of hydrogen, —I, —Br, —Cl and —F; $R_2$ is $C_1$-$C_6$ alkyl; $Ar_1$ is thiazolyl, unsubstituted or substituted with one substituent selected from the group consisting of —I, —Br, —Cl, and —F; Y is O; $Ar_2$ is formula (c) wherein $Z_5$, $Z_6$ and $Z_7$ are C($R_{102}$); $R_{102}$ is hydrogen; $W_1$ and $W_2$ are each —$CH_2$—; and Z is N($R_6$)($R_7$); wherein $R_6$ is hydrogen, and $R_7$ is selected from the group consisting of —C(O)O($C_1$-$C_6$ alkyl), —C(O)$NH_2$, —C(O)N(H)($C_1$-$C_6$ alkyl) and —C(O)($C_1$-$C_6$ alkyl).

Another aspect of the invention relates to compounds of formula (I), or a pharmaceutically acceptable salt, prodrug, salt of a prodrug, or a combination thereof, wherein $Ar_3$ is

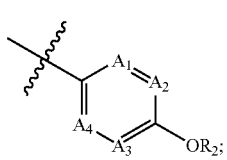
(f)

$A_1$, $A_2$, $A_3$ and $A_4$ are —C($R_v$)—, $R_v$ is selected from the group consisting of hydrogen, —I, —Br, —Cl, and —F; $R_2$ is selected from the group consisting of methyl, ethyl, isopropyl, and 2-methylpropyl; $Ar_1$ is selected from the group consisting of phenyl, pyridinyl, thienyl, furanyl, thiazolyl, and 1,3,4-thiadiazolyl; each of which is independently unsubsti tuted or substituted with one substituent selected from the group consisting of —I, —Br, —Cl, and —F; Y is O; Ar$_2$ is

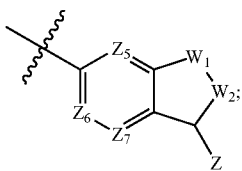

(c)

Z$_5$, Z$_6$ and Z$_7$ are C(H); W$_1$ is CH$_2$; W$_2$ is CH$_2$; and Z is N(R$_6$)(R$_7$); wherein R$_6$ is hydrogen or methyl, and R$_7$ is selected from the group consisting of —C(O)O-methyl, —C(O)NH$_2$, —C(O)N(H)(methyl); and —C(O)methyl. Particularly; the invention directs to compounds of formula (I) wherein Ar$_3$ is formula (f) wherein A$_1$, A$_2$, A$_3$ and A$_4$ are —C(R$_v$)—, R$_v$ is selected from the group consisting of hydrogen, —I, —Br, —Cl, and —F; R$_2$ is selected from the group consisting of methyl and isopropyl; Ar$_1$ is thiazolyl, unsubstituted or substituted with one substituent selected from the group consisting of —I, —Br, —Cl, and —F; Y is O; Ar$_2$ is formula (c) wherein Z$_5$, Z$_6$ and Z$_7$ are C(H); W$_1$ is CH$_2$; W$_2$ is CH$_2$; and Z is N(R$_6$)(R$_7$); wherein R$_6$ is hydrogen, and R$_7$ is selected from the group consisting of —C(O)O-methyl, —C(O)NH$_2$, —C(O)N(H)(methyl); and —C(O)methyl.

One embodiment of the invention are compounds of formula (Ib), or a pharmaceutically acceptable salt, prodrug, salt of a prodrug, or a combination thereof,

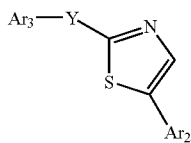

wherein Ar$_3$, Y, and Ar$_2$ are as defined in formula (I). It is understood that embodiments of Ar$_3$, Y and Ar$_2$ and combinations of embodiments, including particular, preferred, more preferred and most preferred embodiments as described in formula (I) are also contemplated for compounds of formula (Ib).

Accordingly, one aspect of the invention relates to compounds of formula (Ib), or a pharmaceutically acceptable salt, prodrug, salt of a prodrug, or a combination thereof, wherein Ar$_3$ is formula (f) wherein A$_1$, A$_2$, A$_3$ and A$_4$ are —C(R$_v$)—, or one of A$_1$, A$_2$, A$_3$ and A$_4$ is N, and the others are —C(R$_v$)— wherein R$_v$ is selected from the group consisting of hydrogen, —I, —Br, —Cl and —F; Y is —O—, Ar$_2$ is of formula (a), (b), (c), (d) or (e) wherein R$_2$, Z$_1$, Z$_2$, Z$_3$, Z$_4$, Z$_5$, Z$_6$, Z$_7$, W$_1$, W$_2$, Z and R are as defined in formula (I). Particularly, Ar$_3$ is formula (f) wherein A$_1$, A$_2$, A$_3$ and A$_4$ are —C(R$_v$)—, or one of A$_1$, A$_2$, A$_3$ and A$_4$ is N, and the others are —C(R$_v$)— wherein R$_1$ is selected from the group consisting of hydrogen, —I, —Br, —Cl and —F; R$_2$ is C$_1$-C$_6$ alkyl; Y is —O—; Ar$_2$ is of formula (a), (b) or (c), Z$_1$, Z$_2$, Z$_3$, Z$_4$ are C(R$_{101}$), or one of Z$_1$, Z$_2$, Z$_3$, Z$_4$ is N and the others are C(R$_{101}$), wherein R$_{101}$ is hydrogen or C$_1$-C$_6$ alkyl; W$_1$ is CH$_2$, W$_2$ is CH$_2$, R is C$_1$-C$_6$ alkyl or haloalkyl; Z is N(R$_6$)(R$_7$); wherein R$_6$ is hydrogen or C$_1$-C$_6$ alkyl, and R$_7$ is selected from the group consisting of —C(O)O(C$_1$-C$_6$ alkyl), —C(O)NH$_2$, —C(O)N(H)(C$_1$-C$_6$ alkyl) and —C(O)(C$_1$-C$_6$ alkyl). More particularly, Ar$_3$ is formula (f) wherein A$_1$, A$_2$, A$_3$ and A$_4$ are —C(R$_v$)—, wherein R$_v$ is selected from the group consisting of hydrogen, —I, —Br, —Cl and —F; R$_2$ is methyl or, isopropyl; Y is —O—; Ar$_2$ is of formula (a), (b) or (c), Z$_1$, Z$_2$, Z$_3$, Z$_4$ are C(R$_{101}$), or one of Z$_1$, Z$_2$, Z$_3$, Z$_4$ is N and the others are C(R$_{101}$), wherein R$_{101}$ is hydrogen; W$_1$ is CH$_2$, W$_2$ is CH$_2$, R is methyl or trifluoromethyl; Z is N(R$_6$)(R$_7$); wherein R$_6$ is hydrogen and R$_7$ is selected from the group consisting of —C(O)Omethyl, —C(O)NH$_2$, —C(O)N(H)(methyl) and —C(O)methyl.

Exemplary compounds of the present invention having formula (I) include, but are not limited to, N-(1-{4-[2-(4-isopropoxyphenoxy)-1,3-thiazol-5-yl]phenyl}ethyl)acetamide;

N-(1-{4-[2-(4-isopropoxyphenoxy)-1,3-thiazol-5-yl]phenyl}ethyl)urea;

N-{5-[2-(4-isopropoxyphenoxy)-1,3-thiazol-5-yl]-2,3-dihydro-1H-inden-1-yl}acetamide;

N-(1-{5-[2-(4-isopropoxyphenoxy)-1,3-thiazol-5-yl]pyridin-3-yl}ethyl)acetamide;

methyl 1-{5-[2-(4-isopropoxyphenoxy)-1,3-thiazol-5-yl]pyridin-3-yl}ethylcarbamate;

N-(1-{5-[2-(4-isopropoxyphenoxy)-1,3-thiazol-5-yl]pyridin-3-yl}ethyl)-N'-methylurea;

N-(1-{3-[2-(4-isopropoxyphenoxy)-1,3-thiazol-5-yl]phenyl}ethyl)acetamide;

methyl 1-{3-[2-(4-isopropoxyphenoxy)-1,3-thiazol-5-yl]phlenyl}ethyl carbamate;

N-(1-{3-[2-(4-isopropoxyphenoxy)-1,3-thiazol-5-yl]phenyl}ethyl)-N'-methylurea;

N-(1-{3-[2-(4-isopropoxyphenoxy)-1,3-thiazol-5-yl]phenyl}ethyl)urea;

methyl 1-{4-[2-(4-methoxy phenoxy)-1,3-thiazol-5-yl]phenyl}ethylcarbamate;

N-(1-{4-[2-(4-methoxyphenoxy)-1,3-thiazol-5-yl]phenyl}ethyl)urea; and

N-(1-{4-[2-(4-methoxyphenoxy)-1,3-thiazol-5-yl]phenyl}ethyl)acetamide; or a pharmaceutically acceptable salt, prodrug, salt of a prodrug, or a combination thereof.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

The invention also provides pharmaceutical compositions including a therapeutically effective amount of a compound of formula (I) or (Ib) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "therapeutically acceptable carrier," as used herein, means a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media, Inhibition of ACC by the compounds of the present invention can be delayed by using a liquid suspension of crystalline or amorphous material with poor water solubility. The rate of absorption of the compounds depends upon their rate of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution-retarding agent, wetting agent, absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) or (Ib) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

Pharmaceutically acceptable salts are well-known in the art. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsultonate, digluconate, glyceropliosphlate, hemisulfate, heptanoate, hexanoate, formate, isethionate, fumarate, lactate, maleate, methanesulfonate, naphthylenesulftonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulftonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen of formula (I) or (Ib).

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethyl amine, tributlyamine, pyridine, N,N-dimethylaniline, N-methylpiperidine, N-methlylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred Esters of the compounds of formula (I) or (Ib) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to nontoxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) or (Ib) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I) or (Ib), for example, by hydrolysis in blood, A thorough discussion is provided in T, Higuchi and V. Stella, Pro-drugs as Novel Delivery Systems, V. 14 of the A.C.S, Symposium Series, and in Edward B, Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I) or (Ib).

The present invention is also directed to a method of inhibiting acetyl-CoA carboxylase (ACC). By inhibiting ACC, the compounds of the present invention can be useful as therapeutic agents for the treatment or prevention of disorders such as but not limited to metabolic syndrome, type II diabetes, obesity, atherosclerosis and cardiovascular disease. Therefore, according to an embodiment of the present invention compounds of formula (I) or (Ib), can be useful for the treatment of metabolic syndrome, type II diabetes, obesity, atherosclerosis and cardiovascular disease.

Compounds and compositions of the invention are useful for inhibiting the effects of ACC, and more particularly that of ACC1 and ACC2. In particular, the compounds and compositions of the invention can be used for treating and preventing disorders modulated by ACC. Typically, such disorders can be ameliorated by selectively inhibiting the ACC in a mammal, preferably by administering a compound or composition of the invention, either alone or in combination with another active agent, for example, as part of a therapeutic regimen.

The compounds of the invention, including but not limited to those specified in the examples, inhibit ACC. As inhibitors of ACC, the compounds of the invention can be useful for the treatment and prevention of a number of ACC mediated diseases or conditions.

Compounds of the invention are particularly useful for the treatment or prevention of metabolic syndrome, type II diabetes, obesity, atherosclerosis and cardiovascular diseases in humans.

Accordingly, the present invention is directed to a method of inhibiting ACC, including administering a therapeutically effective amount of a compound of formula (I) or (Ib).

The present invention is also directed toward a method of inhibiting ACC-1, including administering a therapeutically effective amount of a compound of formula (U) or (Ib).

The present invention is also directed toward a method of inhibiting ACC-2, including administering a therapeutically effective amount of a compound of formula (I) or (Ib).

Another embodiment of the present invention is directed toward a method of treating metabolic syndrome, including administering a therapeutically effective amount of a compound of formula (I) or (Ib).

Another embodiment of the present invention is directed toward a method of treating type II diabetes, including administering a therapeutically effective amount of a compound of formula (I) or (Ib).

Another embodiment of the present invention is directed toward a method of treating obesity, including administering a therapeutically effective amount of a compound of formula (I) or (Ib).

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I) or (Ib) to effectively ameliorate disorders by inhibiting ACC at a reasonable benefit/risk ratio applicable to any medical treatment. The specific therapeutically effective dose level for any particular patient depends upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of ACC in single or divided doses can be in amounts, for example, from about 0.1 to 50 mg/kg body weight. In a more preferred range, compounds of the present invention inhibit the action of ACC in a single or divided doses from about 1 to 25 mg/kg body weight. Single dose compositions can contain such amounts or submultiple doses thereof of the compounds of the present invention to make up the daily dose. In general, treatment regimens comprise administration to a patient in need of such treatment from about 1 mg to about 1000 mg of the compounds per day in single or multiple doses.

Biological Data

The ACC2 enzymatic assay has been developed using either crude digitonin lysates of hACC2 over expressing HEK 293 cells or recombinant human ACC2 expressed in baculovirus/Sf9 system. In both cases in order to increase the expression and solubility of the protein, a chimeric version of ACC2 ("mito-minus"), in which the N-terminal transmembrane domain (1-275 aa's of ACC2) was replaced with the corresponding ACC1 sequence (1-133 aa's). The enzymatic assay measures ACC mediated incorporation of [$^{14}$C] CO2 into [$^{14}$C]-Malonyl CoA. Mono-Avidin purified rat liver ACC1 was used as ACC1 enzyme source for the ACC-1 activity assay. The assay was preformed in 40 μL reaction in a 96-well plate format. The 1× assay buffer contains 50 mM Hepes/NaOH, pH 7.5, 10 mM citrate, 20 mM $MgCl_2$ and 0.075% BSA. First, 20 μL, of test compounds was dissolved in 1% DMSO in 1× assay buffer was dispensed into 96-well. Then, 10 μL of enzyme in 1× assay buffer was dispensed. The reaction was initiated by adding the following substrate mixture in 1× assay buffer: 2 mM ATP, 1 mM acetyl-CoA, and 17.6 mM $NaHCO_3$ (0.12 μCi). The reaction was carried out at room temperature for 40 minutes and the reaction was terminated by adding 50 μL of 1N HCl. The plate was air-dried in a fume hood at room temperature overnight. 20 μL of distilled water was added followed by adding 150 μL of SuperMix liquid scintillation fluid (PerkinElmer). The radioactivity was determined in PerkinElmer microbeta after vigorous shaking. The IC50 value was calculated from 8 dose response curve of test compounds.

TABLE 1

Inhibition of ACC1 and ACC2 Enzymatic Activities

| ACC1 IC50 (μM) | ACC2 IC50 (μM) |
|---|---|
| >30 | 1.3 |
| 4.8 | 0.82 |
| >30 | 7.9 |
| 6.2 | 1.5 |
| 1.0 | 0.23 |
| >30 | 0.26 |
| >30 | 1.9 |
| 3.9 | 1.4 |
| >30 | 1.9 |
| 0.24 | 0.049 |
| 1.7 | 0.31 |
| 3.2 | 0.31 |
| 0.73 | 0.88 |

Dysregulation of fatty acids metabolism contributes to decreased insulin sensitivity and the development of metabolic syndrome. ACC is known to modulate fatty acid synthesis and fatty acid oxidation in insulin responsive tissues such as liver, adipose and skeletal muscles. The ACC inhibitors of the present invention have the potential to decrease de novo lipid synthesis and increase fat oxidation in vivo. Therefore, these chemotypes represent a novel method to treat insulin resistance/type 2 diabetes, as well as obesity, hypertension and hyperlipidemia.

Synthetic Methods

The compounds and processes of the present invention will be better understood in connection with the following synthetic schemes, which together illustrate the methods by which the compounds of the invention can be prepared. The synthesis of compounds of formula (I) or (Ib) wherein the groups R, $R_4$, $R_7$, $Ar_1$, $Ar_2$, $Ar_3$, and Y are as defined above unless otherwise noted, are exemplified in Schemes 1-4.

Starting materials can be obtained from commercial sources or prepared by well-established literature methods known to those of ordinary skill in the art.

This invention is intended to encompass compounds having formula (I) or (Ib) when prepared by synthetic processes or by metabolic processes. Preparation of the compounds of the invention by metabolic processes include those occurring in the human or animal body (in vivo) or processes occurring in vitro.

As used in the descriptions of the schemes and the examples, certain abbreviations are intended to have the following meanings: DMSO for dimethylsulfoxide; and HPLC for high pressure liquid chromatography.

Scheme 1

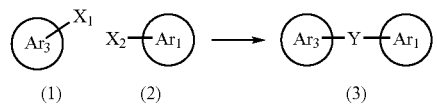

Compounds of formula (3) wherein $Ar_1$, $Ar_3$ are as defined in formula (I) and Y is —O—, —N(alkyl)-, —N(H)— and —S—, can be prepared by reacting compounds of formula (1) wherein $X_1$ is Y—H, with halides of formula (2) wherein $X_2$ is Br, Cl, F or triflate, in the presence of a base such as, but not limited to sodium hydride or potassium carbonate, and optionally in the presence of 18-crown-6. The reaction can generally be performed in a solvent such as, but not limited to, N,N-dimethylformamide or dimethylsulfoxide, at a temperature from about room temperature to about 180° C. It is appreciated compounds of formula (3) can also be obtained from the reaction of formula (1) wherein $X_1$ is Br, Cl, F or triflate, and compounds of formula (2) wherein $X_2$ is Y—H.

Alternatively, the transformation can also be effected in the presence of a metal catalyst such as, but not limited to, copper metal, CuI, palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, sodium tert-butoxide, cesium carbonate, or sodium hydride. The reaction is generally performed at a temperature from about room temperature to about 180° C., in a solvent such as, but not limited to, toluene or N,N-dimethylformamide Scheme 2

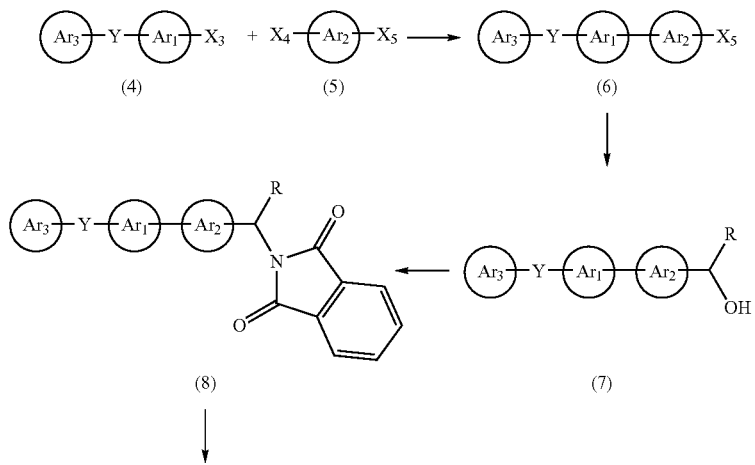

-continued

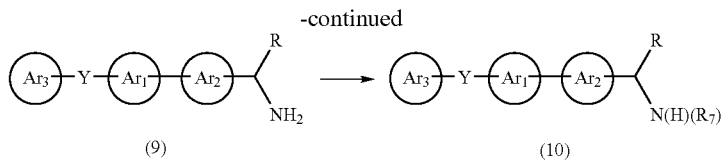

(9) → (10)

Compounds of formula (8) and (10) wherein $Ar_2$ is phenyl or a monocyclic, six-membered heteroaryl, unsubstituted or substituted as defined in formula (I), Y is —O—, —N(alkyl)-, —N(H)— and —S—, and $Ar_1$, $Ar_3$, R and $R_7$ are as defined in formula (I) can be prepared as outlined in Scheme 2.

Stannanes of formula (4) wherein $X_3$ is —Sn(alkyl)$_3$ can be reacted with compounds of formula (5) wherein $X_4$ is Cl, Br or triflate, and $X_5$ is hydrogen, formyl, or RC(O)—; in the presence of a palladium source such as tris(dibenzylidineacetone)dipalladium, tetrakis(triphenylphosphine)palladium (0), optionally in the presence of a ligand such as tri(2-furyl) phosphine or triphenylarsine, to provide compounds of formula (6) wherein $X_5$ is hydrogen, formyl, or RC(O)—. The reaction is generally conducted in a solvent such as N,N-dimethylformamide at a temperature from about 25° C. to about 150° C. It is appreciated compounds of formula (6) can also be obtained from the reaction of stannanes of formula (5) wherein $X_4$ is —Sn(alkyl)$_3$ and compounds of formula (4) wherein $X_3$ is Cl, Br or triflate.

Stannanes of formula (4) or (5) can be purchased or prepared from heteroarylhalides, heteroaryltriflates, arylhalides or aryltriflates by reaction with hexa-alkyl distannanes of formula ((alkyl)$_3$Sn)$_2$ in the presence of a palladium source like tetrakis(triphenylphosphine)palladium(0). Alternatively, stannanes of formula (4) or (5) can be obtained from metal-halogen exchange of compounds of formula (4) or (5) wherein $X_3$ or $X_4$ is bromide, with n-butyl lithium at about −78° C., followed by reaction with tributyl tin halide at a temperature from about −78° C. to about room temperature, in a solvent such as tetrahydrofuran.

Conversion of compounds of formula (6) wherein $X_5$ is hydrogen to compounds of formula (6) wherein $X_5$ is formyl group can be effected by employing n-butyl lithium followed by treatment with a formylation agent such as, but not limited to, N-formylmorpholine.

Compounds of formula (6) wherein $X_5$ is hydrogen can be converted to compounds of formula (7) by treatment with a lithium base such as, but not limited to, n-butyl lithium in a solvent such as, but not limited to, tetrahydrofuran or dichloromethane, followed by aldehydes of formula RCHO.

Treatment of compounds of formula (6) wherein $X_5$ is formyl with trimethyl(trifluoromethyl)silane and tetrabutylammonium fluoride in a solvent such as, but not limited to, tetrahydrofuran, provides compounds of formula (7) wherein R is trifluoromethyl.

Reduction of compounds of formula (6) wherein $X_5$ is $R_1C(O)$— with a reducing agent such as, but not limited to, sodium borohydride in a mixture of solvent of methanol and tetrahydrofuran affords to alcohols of formula (7).

Treatment of alcohols of formula (7) with phthalimide, triphenylphosphine, and diethyl azodicarboxylate in a solvent such as, but not limited to, tetrahydrofuran, at room temperature provides compounds of formula (8).

Treatment of compounds of formula (8) with hydrazine, in a solvent such as, but not limited to, dichloromethane, ethanol, or a mixture thereof at a temperature from about room temperature to about the reflux temperature of the solvent employed, provides primary amines of formula (9).

Reaction of the primary amines of formula (9) with trichloroacetyl isocyanate in a solvent such as dichloromethane and the like, at room temperature, followed by refluxing in methanol in catalytic amount of sodium carbonate and water, affords compounds of formula (10) wherein $R_7$ is —C(O) $NH_2$. Ureas of formula (10) wherein $R_7$ is —C(O)N(H)($R_{11}$) and $R_{11}$ is alkyl, haloalkyl, —$R_4$ and -alkylenyl-$R_4$, and $R_4$ is as defined in formula (I), can be facilitated by treatment of (9) with isocyanates of formula $R_{11}$NCO, in a solvent such as dichloromethane and the like, at about room temperature.

Reaction of the primary amines of formula (9) with chloroformates of formula ClC(O)OR$_8$ at room temperature in the presence of an organic base such as, but not limited to, triethylamine or diisopropyl ethyl amine, and in a solvent such as, but not limited to, dichloromethane, affords carbamates of formula (10) wherein $R_7$ is —C(O)OR$_8$.

The primary amines of formula (9) can also be derivatized by acylating the amines with acetic anhydride or acyl halides of formula $R_8C(O)X$ wherein X is Br or Cl; and $R_8$ is as defined in formula (I), in the presence of an organic base such as, but not limited to, triethylamine or diisopropyl ethyl amine. The reaction is generally performed in a solvent such as, but not limited to, dichloromethane or tetrahydrofuran, at about room temperature.

Sulfonamides of formula (10) wherein $R_7$ is —S(O)$_2$R$_8$ can be prepared from compounds of formula (9) by treatment with sulfonyl chlorides of formula $R_8SO_2Cl$ in the presence of an organic base such as, but not limited to, triethylamine or diisopropyl ethyl amine.

Scheme 3

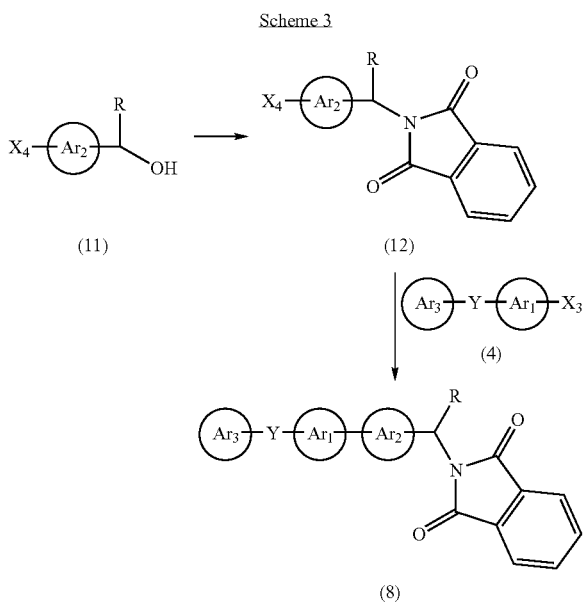

Alternatively, compounds of formula (8) wherein $Ar_2$ is phenyl or a monocyclic, six-membered heteroaryl, unsubstituted or substituted as defined in formula (I), Y is —O—, —N(alkyl)-, —N(H)— and —S—, $Ar_1$, $Ar_3$, and R are as defined in formula (I) can be prepared from alcohols of formula (11) as shown in Scheme 3. Alcohols of formula (11) wherein $X_4$ is Cl, Br or triflate can be purchased or prepared using known methodologies. When treated with phthalimide, triphenylphosphline, and diethyl azodicarboxylate in a solvent such as, but not limited to, tetrahydrofuran, at room temperature, compounds of formula (11) can be converted to compounds of formula (12). Reaction of compounds of formula (12) wherein $X_4$ is Cl, Br or triflate with compounds of formula (4) wherein $X_3$ is —Sn(alkyl)$_3$, using the reaction conditions as outlined in Scheme 2 for the conversion of compounds of formula (4) to compounds of formula (6), provides compounds of formula (8).

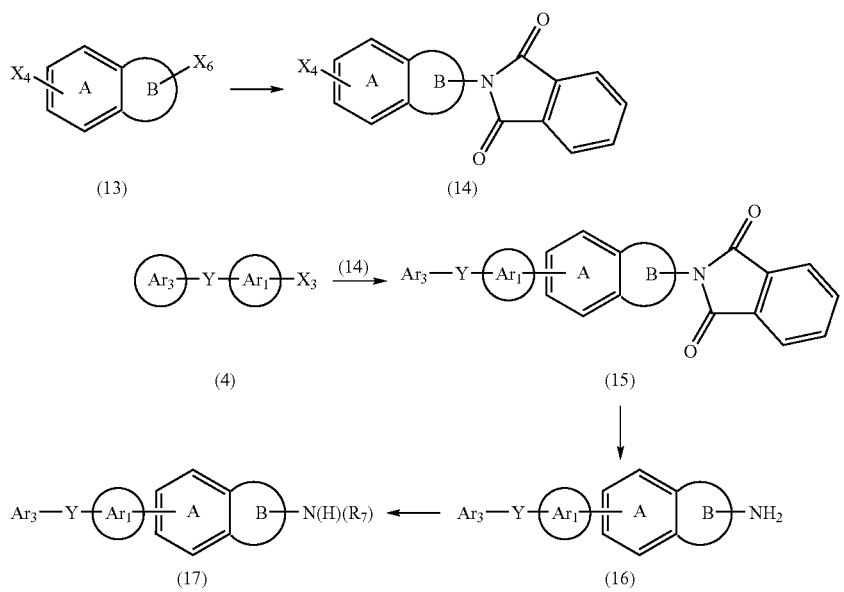

Compounds of formula (17) wherein ring A is phenyl or monocyclic six membered heteroaryl as defined in formula (I), ring B is a monocyclic, five or six membered cycloalkyl or heterocycle as defined in formula (I), Y is —O—, —N(alkyl)-, —N(H)— and —S—, and $Ar_1$, $Ar_3$ and $R_7$ are as defined in formula (I) can be prepared as shown in Scheme 4.

Compounds of formula (14) wherein Se is Br, Cl or triflate can be prepared from compounds of formula (13) wherein X is Br, Cl or triflate, and $X_6$ is =O, by (a) reducing with a reducing agent such as sodium borohydride and the like, in a mixture of solvent of methanol and tetrahydrofuran to provide compounds of formula wherein $X_6$ is OH; and (b) reacting the product of step (a) with phthalimide, triphenylphosphine, and diethyl azodicarboxylate in a solvent such as, but not limited to, tetrahydrofuran, at room temperature.

Compounds of formula (4) can be converted to amines of formula (16) by (a) reacting with compounds of formula (14), and (b) deprotection of the phthalimide; using the reaction conditions as described in Scheme 2.

Amines of formula (16) can be further derivatized to the corresponding ureas, carbamates, amides and sulfonamides respectively using reaction conditions as shown in Scheme 2.

The present invention will now be described in connection with certain preferred embodiments which are not intended to limit its scope. On the contrary, the present invention covers all alternatives, modifications, and equivalents as can be included within the scope of the claims. Routine experimentation, including appropriate manipulation of the reaction conditions, solvents and reagents used, and sequence of the synthetic route, protection of any chemical functionality that can not be compatible with the reaction conditions, and deprotection thereafter are included in the scope of the invention Synthesis of the compounds of formula (I) or (Ib) can be accomplished by methods analogous to those described above and in the following examples. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.06 (developed by Advanced Chemistry Development, Inc., Toronto, ON, Canada) or were given names consistent with ACD nomenclature.

EXAMPLES

Example 1

N-(1-{4-[2-(4-isopropoxyphenoxy)-1,3-thiazol-5-yl]phenyl}ethyl)acetamide

Example 1A

4-Isopropoxy-phenol

To a solution of hydroquinone (55.7 g, 0.5 mol) and 2-iodopropane (57.5 g, 0.33 mol) in ethanol was added a solution of potassium hydroxide (78.5 g, 0.5 mol) in water (100 mL). The dark brown solution was then refluxed for 16 hours. The solution was concentrated and the remaining aqueous phase was acidified with 2N HCl and extracted with ethyl acetate (3×200 mL). The combined organic layers were washed with brine, dried over magnesium sulfate and filtered. The filtrate was concentrated to give over 70 g of crude material, which was triturated with methylene chloride and filtered. The filtrate was concentrated and purified on silica gel (5~35% ethyl acetate in hexane) to give 23.0 g of the title compound (46% yield). $^1$H NMR (300 MHz, CDCl$_3$) δ ppm 1.30 (d, J=5.88 Hz, 6 H) 4.30-4.50 (m, 1 H) 4.78 (s, 1 H) 6.66-6.86 (m, 4 H). MS (ESI): m/z 151 (M−H).

Example 1B 2-(4-Isopropoxy-phenoxy)-thiazole

A mixture of Example 1A (15.5 g, 0.1 mol), 2-bromothiazole (18.2 g, 0.11 mol) and potassium carbonate (15.2 g, 0.11 mol) in dimethylsulfoxide was heated at 160° C. under nitrogen for 6 hours. It was then cooled and treated with water, and the aqueous phase was extracted with methylene chloride. The organic layer washed with brine, dried (MgSO$_4$) and concentrated to give 27.5 g of the crude material which was purified on silica gel (5~35% ethyl acetate in hexane) to afford 21.5 g of the title compound (91% yield) $^1$H NMR (500 MHz, CDCl$_3$) δ ppm 1.32-1.36 (m, 6 H) 1.34 (none, 6 H) 1.34 (none, 5 H) 4.45-4.57 (m, 1 H) 6.76 (d, J=3.91 Hz, 1 H) 6.87-6.93 (m, 2 H) 7.15-7.20 (m, 2 H) 7.21 (d, J=3.91 Hz, 1 H). MS (ESI): m/z 236 (M−H).

Example 1C 2-(4-Isopropoxy-phenoxy)-5-tributylstannanyl-thiazole

To a solution of Example 1B (2.4 g, 0.01 mol) in dry tetrahydrofuran was added n-butyl lithium (4.4 mL, 2.5 M in hexane) at −78° C. drop wise. After stirring at this temperature for 1 h, tributyltin chloride (3.0 mL, 0.011 mol) was added slowly to the mixture. The brown solution was then stirred for 3 hours while warming up to room temperature. Water was added and the solution was extracted with ethyl acetate. The organic layer washed with saturated NH$_4$Cl, brine, and then dried over magnesium sulfate. The solution was concentrated and the crude was purified on a silica gel flash column, eluting with 5-30% EtOAc in hexane, to give 4.85 g of the title compound (93% yield), $^1$H NMR (300 MHz, CDCl$_3$) δ ppm 0.77-1.74 (m, 33 H) 4.40-4.63 (m, 1 H) 6.84-6.95 (m, 2 H) 7.12 (s, 1 H) 7.14-7.23 (m, 2 H). MS (ESI), m/z 526.2 (M+H)$^+$.

Example 1D

2-[1-(4-Bromo-phenyl)-ethyl]-isoindole-1,3-dione

To a solution of 4-bromo-α-methylbenzylalcohol (3.0 g, 0.015 mol), phthalimide (2.2 g, 0.015 mol) and triphenylphosphine (6.0 g, 0.023 mol) in tetrahydrofuran was added diethyl azodicarboxylate (4.0 g, 0.023 mol) and the reaction mixture was stirred at room temperature for 14 hours. The solution was concentrated and the crude material was purified on silica gel (10~35% ethyl acetate in hexane) to give 2.93 g of the title compound (60% yield) $^1$H NMR (300 MHz, CDCl$_3$) δ ppm 1.90 (d, J=7.35 Hz, 3 H) 5.52 (q, J=7.11 Hz, 1 H) 7.34-7.41 (m, 2 H) 7.41-7.50 (m, 2 H) 7.65-7.74 (m, 2 H) 7.76-7.86 (m, 2 H) MS (ESI), m/z 404.0 (M+H)$^+$.

Example 1E 2-(1-{4-[2-(4-isopropoxyphenoxy)-1,3-thiazol-5-yl]phenyl}ethyl)-1H-isoindole-1,3(2H)-dione A mixture of Example 1C (1.85 g, 0.0035 mol), Example 1D (1.11 g, 0.0034 mol) and tetrakis(triphenyl)phosphine (0.23 g, 0.0002 mol) in N,N-dimethylformamide (20 mL) was heated at 60° C. overnight. The mixture was cooled to room temperature, and concentrated. The residue was purified on silica gel (5~25% ethyl acetate in hexane) to give 0.7 g of product as an off-white solid (42% yield). $^1$H NMR (300 MHz, CDCl$_3$) δ ppm 1.35 (d, J=6.25 Hz, 6 H) 1.92 (d, J=7.35 Hz, 3 H) 4.44-4.60 (m, 1 H) 5.56 (q, J=7.35 Hz, 1 H) 6.87-6.95 (m, 2 H) 7.15-7.23 (m, 2 H) 7.36 (s, 1 H) 7.36-7.42 (m, 2 H) 7.45-7.5.3 (m, 2 H) 7.66-7.74 (m, 2 H) 7.76-7.85 (m, 2 H). MS (ESI), m/z 485.1 (M+H)$^+$.

Example 1F

1-{4-[2-(4-isopropoxyphenoxy)-1,3-thiazol-5-yl]phenyl}ethanamine

To a solution of Example 1E (0.65 g, 0.0013 mol) in a mixture of methylene chloride (20 mL) and ethanol (2 mL) was added hydrazine monohydrate (0.66 g, 0.013 mol) and the mixture was refluxed under nitrogen for 2 hours. The white suspension was cooled to room temperature, concentrated, dissolved in methylene chloride, and filtered. The filtrate was concentrated to give 0.46 g of the title compound, which was used without further purification. $^1$H NMR (300 MHz, CDCl$_3$) δ ppm 1.35 (d, J=5.88 Hz, 6 H) 139 (d, J=6.62 Hz, 3 H) 4.13 (q, J=6.62 Hz, 1 H) 4.44-4.62 (m, 1 H) 6.86-6.98 (m, 2 H) 7.16-7.25 (m, 2 H) 7.30-7.44 (m, 5 H). MS (ESI), m/z 337.7 (M−17)$^+$.

Example 1G

N-(1-{4-[2-(4-isopropoxyphenoxy)-1,3-thiazol-5-yl]phenyl}ethyl)acetamide

To a solution of Example 1F (0.15 g, 0.0004 mol) and excess triethylamine (2 mL) in methylene chloride (5 mL) was added excess acetic anhydride (1 mL) and the mixture was stirred at room temperature for 15 minutes. After quenching with methanol (5 mL), the solvent was concentrated and the residue was purified on silica gel (50~75% ethyl acetate in hexane) to give 0.12 g of the title compound (76% yield). $^1$H NMR (300 MHz, CDCl$_3$) δ ppm 1.35 (d, J=6.25 Hz, 6 H) 1.49 (d, J=6.99 Hz, 3 H) 2.00 (s, 3 H) 4.44-4.60 (m, 1 H) 5.06-5.20 (m, 1 H) 5.67 (d, J=6.99 Hz, 1 H) 6.87-6.97 (m, 2 H) 7.16-7.24 (m, 2 H) 7.27-7.34 (m, 2 H) 7.37 (s, 1 H) 7.38-7.44 (m, 2 H). MS (ESI), m/z 396.9 (M+H)$^+$.

Example 2

N-(1-{4-[2-(4-isopropoxyphenoxy)-1,3-thiazol-5-yl]phenyl}ethyl)urea

To a solution of Example 1F (0.15 g, 0.0004 mol) in methylene chloride (5 mL) was added trichloroacetyl isocyanate (0.08 mL, 0.0006 mol) and the mixture was stirred at room temperature for 15 minutes, and concentrated. The residue was dissolved in methanol (10 mL) and refluxed with a few drops of saturated sodium carbonate solution for 0.5 hours. The mixture was cooled to room temperature, concentrated to dryness and triturated with methanol (15 mL) and water (2 mL) to give 0.15 g of the title compound (88% yield). $^1$H NMR (300 MHz, DMSO-d$_6$) δ ppm 1.23-1.34 (m, 9 H) 4.55-4.75 (m, 2 H) 5.42 (s, 2 H) 6.44 (d, J=8.09 Hz, 1 H) 6.97-7.05 (m, 2 H) 7.25-7.36 (m, 4 H) 7.49 (d, J=8.09 Hz, 2 H) 7.65 (s, 1 H). MS (ESI), m/z 397.9 (M+H)$^+$.

Example 3

N-{5-[2-(4-isopropoxyphenoxy)-1,3-thiazol-5-yl]-2, 3-dihydro-1H-inden-1-yl}acetamide

Example 3A

5-Bromo-indan-1-ol

To a solution of 5-bromoindanone (2.2 g, 0.01 mol) in a mixture of methanol (50 mL) and tetrahydrofuran (10 mL) was added sodium borohydride (0.78 g, 0.02 mol) and the reaction mixture was stirred at room temperature overnight. The solution was concentrated and the residue was partitioned between water and ethyl acetate. The organic layer was washed with brine, dried over magnesium sulfate and filtered. The filtrate was concentrated to give 2.15 g of crude material. $^1$H NMR (300 MHz, CDCl$_3$) 6 ppm 157 (s, 1 H) 1.87-2.02 (m, 1 H) 2.40-2.59 (m, 1 H) 2.73-2.88 (m, 1 H) 2.95-3.11 (m, 1 H) 5.12-5.25 (m, 1 H) 7.29 (s, 1 H) 7.32-7.43 (m, 2 H). MS (ESI), m/z 416.0 (M+205)$^+$.

Example 3B 2-(5-bromo-2,3-dihydro-1H-inden-1-yl)-1H-isoindole-1,3 (2H)-dione The title compound was prepared as described in Example 1D, substituting Example 3A for 4-bromo-α-methylbenzylalcohol. The crude material was purified on silica gel (10~35% ethyl acetate in hexane) to give 1.55 g of the title compound (45% yield). $^1$H NMR (300 MHz, CDCl$_3$) δ ppm 2.39-2.63 (m, 2 H) 2.90-3.08 (m, 1 H) 3.29-3.44 (m, 1 H) 5.81 (dd, J=8.82, 6.62 Hz, 1 H) 6.97 (d, J=8.09 Hz, 1 H) 7.22-7.31 (m, 1 H) 7.44 (s, 1 H) 7.67-7.77 (m, 2 H) 7.77-7.87 (m, 2 H). MS (ESI), m/z 360.1 (M+F)$^+$.

Example 3C

2-{5-[2-(4-isopropoxyphenoxy)-1,3-thiazol-5-yl]-2, 3-dihydro-1H-inden-1-yl}-1H-isoindole-1,3(2H)-dione The title compound was prepared as described in Example 1E, substituting Example 3B for 1D. After the N,N-dimethylformamide was removed, the crude was triturated with hexane (100 mL) and ether (5 mL) to give the title compound (91% yield). $^1$H NMR (300 MHz, CDCl$_3$) δ ppm 1.29-1.40 (m, 6 H) 2.40-2.66 (m, 2 H) 2.93-3.09 (m, 1 H) 3.28-3.44 (m, 1 H) 4.44-460 (m, 1 H) 5.87 (dd, J=8.82, 6.62 Hz, 1 H) 6.87-6.96 (m, 2 H) 7.08 (d, J=8.09 Hz, 1 H) 7.15-7.23 (m, 2 H) 7.24 (d, J=1.84 Hz, 1 H) 7.34-7.39 (m, 2 H) 7.65-7.76 (m, 2 H) 7.78-7.87 (m, 2 H), MS (ESI), m/z 497.0 (M+H)$^+$.

Example 3D

N-{5-[2-(4-isopropoxyphenoxy)-1,3-thiazol-5-yl]-2, 3-dihydro-1H-inden-1-yl}acetamide A mixture of Example 3C (1.95 g, 0.0039 mol) and hydrazine (1.95 g, 0.039 mol) in dichloromethane and ethanol (10:1) was heated at reflux for 3 hours. The reaction was cooled and filtered, the filtrate was concentrated, and the residue was suspended in dichloromethane and filtered again. The filtrate was evaporated to give 1.58 g of crude product.

To the crude product (0.2 g, 0.00055 mol) and excess triethylamine (2 mL) in dichloromethane was added acetic anhydride (excess, 1 mL) at room temperature and the mixture was stirred for 0.5 hours. After the removal of solvent, the crude was triturated with ethyl acetate and hexane to give 0.1 g of product as a tan solid (44% yield). $^1$H NMR (300 MHz, DMSO-d$_6$) δ ppm 1.28 (d, J=5.88 Hz, 6 H) 1.68-1.83 (m, 1 H) 1.86 (s, 3 H) 2.30-2.44 (m, 1 H) 2.71-2.85 (m, 1 H) 2.86-3.00 (m, 1 H) 4.55-469 (m, 1 H) 5.24 (q, J=7.84 Hz, 1 H) 6.96-7.06 (m, 2 H) 7.19 (d, J=8.09 Hz, 1 H) 7.27-7.33 (m, 2 H) 7.34-7.39 (m, 1 H) 7.43 (s, 1 H) 7.66 (s, 1 H) 8.22 (d, J=8.09 Hz, 1 H). MS (ESI), m/z 409.0 (M+H)$^+$.

Example 4

N-(1-{5-[2-(4-isopropoxyphenoxy)-1,3-thiazol-5-yl] pyridin-3-yl}ethyl)acetamide

Example 4A 1-(5-bromopyridin-3-yl)ethanol

The title compound was prepared as described in Example 3A, substituting 3-acetyl-5-bromopyridine for 5-bromoindanone (80% yield). $^1$H NMR (300 MHz, CDCl$_3$) δ ppm 1.54 (t, J=6.25 Hz, 3 H) 4.95 (q, J=6.37 Hz, 1 H) 7.90 (t, J=2.02 Hz, 1 H) 8.53 (d, J=24.27 Hz, 2 H). MS (ESI), m/z 203.9 (M+H)$^+$.

Example 4B

2-[-(5-bromopyridin-3-yl)ethyl]-1H-isoindole-1,3 (2H)-dione

The title compound was prepared as described in Example 1D, substituting Example 4A for 4-bromo-α-methylbenzylalcohol (86%). $^1$H NMR (300 MHz, CDCl$_3$) δ ppm 1.93 (d, J=7.35 Hz, 3 H) 5.57 (q, J=7.35 Hz, 1 H) 7.66-7.79 (m, 2 H) 7.80-7.92 (m, 3 H) 7.88 (none, 1 H) 7.99-8.11 (m, 1 H) 8.61 (dd, J=13.79, 1.65 Hz, 1 H). MS (ESI), m/Z 330.7 (M)$^+$.

Example 4C 2-(1-{5-[2-(4-isopropoxyphenoxy)-1,3-thiazol-5-yl] pyridin-3-yl}ethyl)-1H-isoindole-1,3(2H)-dione The title compound was prepared as described in Example 1E, substituting Example 413 for Example 1D (93%). $^1$H NMR (300 MHz, CDCl$_3$) δ ppm 1.36 (d, J=6.25 Hz, 6 H) 1.95 (d, J=7.35 Hz, 3 H) 4.47-4.61 (m, 1 H) 5.60 (q, J=7.35 Hz, 1 H) 6.88-6.98 (m, 2 H) 7.17-7.24 (m, 2 H) 7.46 (s, 1 H) 7.67-7.75 (m, 2 H) 7.79-7.86 (m, 2 H) 7.89 (t, J=2.21 Hz, 1 H) 8.61 (d, J=2.21 Hz, 1 H) 8.63 (d, J=1.84 Hz, 1 H)$_3$ MS (ESI), m/z 518.2 (M+33)$^+$.

Example 4D

1-{5-[2-(4-isopropoxyphenoxy)-1,3-thiazol-5-yl] pyridin-3-yl}ethanamine

The title compound was prepared as described in Example 1F, substituting Example 4C for Example 1E. $^1$H NMR (300 MHz, CDCl$_3$) δ ppm 1.36 (d, J=5.88 Hz, 6 H) 1.42 (d, J=6.62 Hz, 3 H) 1.67 (s, 2 H) 4.22 (q, J=6.50 Hz, 1 H) 4.46-4.61 (m, 1 H) 6.89-6.98 (m, 2 H) 7.17-725 (m, 2 H) 7.47 (s, 1 H) 7.75 (t, J=2.21 Hz, 1 H) 8.49 (d, J=1.84 Hz, 1 H) 8.59 (d, J=2.21 Hz, 1 H). MS (ESI), m/z 356.1 (M+H)+.

Example 4E

N-(1-{5-[2-(4-isopropoxyphenoxy)-1,3-thiazol-5-yl]pyridin-3-yl}ethyl)acetamide

The title compound was prepared as described in Example 1G, substituting Example 4D for Example 1F (84%), $^1$H NMR (300 MHz, DMSO-d$_6$) δ ppm 1.29 (d, J=5.88 Hz, 6 H) 1.36 (d, J=6.99 Hz, 3 H) 1.84 (s, 3 H) 4.55-4.70 (m, 1 H) 4.87-5.02 (m, 1 H) 6.97-7.07 (m, 2 H) 7.29-7.38 (m, 2 H) 7.82 (t, J=2.02 Hz, 1 H) 7.84 (s, 1 H) 8.36 (d, J=8.09 Hz, 1 H) 8.44 (d, J=1.84 Hz, 1 H) 8.69 (d, J=2.21 Hz, 1 H). MS (ESI), m/z 398.1 (M+H)+.

Example 5 methyl 1-{5-[2-(4-isopropoxyphenoxy)-1,3-thiazol-5-yl]pyridin-3-yl}ethylcarbamate To a solution of Example 49 (0.32 g, 0.0009 mol) in dry tetrahydrofuran (15 mL) was added excess diisopropylethylamine (2 mL), followed by methyl chloroformate (0.13 g, 0.0014 mol) and the mixture was stirred at room temperature for 0.5 hours. After quenching with methanol (10 mL), the solvent was concentrated and tme residue was purified on silica gel (30~75% ethyl acetate in hexane) to give 0.29 g of the title compound (78% yield). $^1$H NMR (300 MHz, DMSO-d$_6$) δ ppm 1.29 (d, J=5.88 Hz, 6 H) 1.36 (d, J=6.99 Hz, 3 H) 3.51 (s, 3 H) 4.55-4.80 (m, 2 H) 6.97-7.08 (m, 2 H) 7.26-7.41 (m, 2 H) 7.77 (d, J=7.72 Hz, 1 H) 7.82-7.89 (m, 2 H) 8.45 (d, J=1.84 Hz, 1 H) 8.71 (d, j=2.21 Hz, 1 H). MS (ESI), m/z 414.1 (M+1)+.

Example 6

N-(1-{5-[2-(4-isopropoxyphenoxy)-1,3-thiazol-5-yl]pyridin-3-yl}ethyl)-N'-methylurea To a solution of Example 4D (0.32 g, 0.0009 mol) in methylene chloride (15 mL) was added excess methyl isocyanate (0.25 mL) and the mixture was stirred at room temperature for 0.5 hours. After quenching with methanol (10 mL), the solvent was concentrated and the residue was purified on silica gel (75~100% ethyl acetate in hexane) to give 0.28 g of the title compound (76% yield). $^1$H NMR (300 MHz, DMSO-d$_6$) δ ppm 1.29 (d, J=6.25 Hz, 6 H) 1.34 (d, J=6.99 Hz, 3 H) 2.51 (d, J=4.78 Hz, 3 H) 4.55-4.70 (m, 1 H) 4.71-4.85 (m, 1 H) 5.72 (q, J=4.41 Hz, 1 H) 6.48 (d, J=8.09 Hz, 1 H) 6.96-7.07 (m, 2 H) 7.28-7.39 (m, 2 H) 7.77-7.81 (m, 1 H) 7.83 (s, 1 H) 8.42 (d, J=1.84 Hz, 1 H) 8.67 (d, J=2.21 Hz, 1 H). MS (ESI), m/z 413.1 (M+1)+.

Example 7

N-(1-{3-[2-(4-isopropoxyphenoxy)-1,3-thiazol-5-yl]phenyl}ethyl)acetamide

Example 7A

2-[1-(3-bromophenyl)ethyl]-1H-isoindole-1,3(2H)-dione

The title compound was prepared as described in Example 1D, substituting 3-bromo-α-methylbenzyl alcohol for 4-bromo-α-methylbenzyl alcohol (70%). $^1$H NMR (300 MHz, CDCl$_3$) δ ppm 1.90 (d, J=7.35 Hz, 6 H) 5.52 (q, J=7.35 Hz, 1 H) 7.20 (t, J=7.91 Hz, 1 H) 7.39 (d, J=8.46 Hz, 1 H) 7.44 (d, J=7.72 Hz, 1 H) 7.64 (s, 1 H) 7.66-7.74 (m, 2 H) 7.77-7.87 (m, 2 H), MS (ESI), m/z 363.9 (M+34)+.

Example 7B 2-(1-{3-[2-(4-isopropoxyphenoxy)-1,3-thiazol-5-yl]phenyl}ethyl)-1H-isoindole-1,3(2H)-dione The title compound was prepared as described in Example 1E, substituting Example 7A for Example 1D (75%). $^1$H NMR (300 MHz, CDCl$_3$) δ ppm 1.36 (d, J=5.88 Hz, 6 H) 1.93 (d, J=7.35 Hz, 3 H) 4.45-4.60 (m, 1 H) 5.56 (q, J=7.11 Hz, 1 H) 6.87-697 (m, 2 H) 7.15-7.24 (m, 2 H) 7.30-7.36 (m, 2 H) 7.39 (s, 1 H) 7.41-7.49 (m, 1 H) 7.55 (s, 1 H) 7.65-7.74 (m, 2 H) 7.76-7.86 (m, 2 H). MS (ESI), m/z 458.1 (M+H)+.

Example 7C

1-{3-[2-(4-isopropoxyphenoxy)-1,3-thiazol-5-yl]phenyl}ethanamine

The title compound was prepared as described in Example 1F, substituting Example 7B for Example 1E. The crude product was used without further purification MS (ESI), m/z 337.7 (M−17)+.

Example 7D

N-(1-{3-[2-(4-isopropoxyphenoxy)-1,3-thiazol-5-yl]phenyl}ethyl)acetamide

The title compound was prepared as described in Example 1G, substituting Example 7C for Example 1F. $^1$H NMR (300 MHz, DMSO-d$_6$) δ ppm 1.29 (d, J=5.88 Hz, 6 H) 1.32 (d, J=6.99 Hz, 3 H) 1.83 (s, 3 H) 4.54-4.69 (m, 1 H) 4.83-4.96 (m, 1 H) 6.96-7.07 (m, 2 H) 7.19-7.27 (m, 1 H) 7.28-7.38 (m, 3 H) 7.40-7.47 (m, 2 H) 7.69 (s, 1 H) 8.30 (d, J=7.72 Hz, 1 H). MS (ESI), m/z 397.1 (M+H)+.

Example 8 methyl 1-{3-[2-(4-isopropoxyphenoxy)-1,3-thiazol-5-yl]phenyl}ethylcarbamate

The title compound was prepared as described in Example 5, substituting Example 7C for Example 4D. $^1$H NMR (300 MHz, DMSO-d$_6$) δ ppm 1.19-1.38 (m, 9 H) 2.51 (d, J=4.78 Hz, 3 H) 4.53-4.81 (m, 2 H) 5.65 (q, J=4.66 Hz, 1 H) 6.40 (d, J=8.09 Hz, 1 H) 6.95-7.07 (m, 2 H) 7.16-7.46 (m, 6 H) 7.18-7.26 (m, 1 H) 7.27-7.49 (m, 5 H) 7.68 (s, 1 H), MS (ESI), m/z 413.3 (M+1)+.

Example 9

N-(1-{3-[2-(4-isopropoxyphenoxy)-1,3-thiazol-5-yl]phenyl}ethyl)-N'-methylurea

The title compound was prepared as described in Example 6, substituting Example 7C for Example 4D. $^1$H NMR (300 MHz, DMSO-d$_6$) δ ppm 1.19-1.38 (m, 9H) 2.51 (d, J=4.78 Hz, 3 H) 4.53-4.81 (m, 2 H) 5.65 (q, J=4.66 Hz, 1 H) 6.40 (d, J=8.09 Hz, 1 H) 6.95-7.07 (m, 2 H) 7.18-7.26 (m, 1 H) 7.27-7.49 (m, 5 H) 7.68 (s, 1 H). MS (ESI) m/z 412.1 (M+1)+.

Example 10

N-(1-{3-[2-(4-isopropoxyphenoxy)-1,3-triazol-5-yl]phenyl}ethyl)urea

The title compound was prepared as described in Example 2, substituting Example 7C for Example 1F. $^1$H NMR (300 MHz, DMSO-$d_6$) δ ppm 1.22-1.36 (m, 9H) 453-4.79 (m, 2 H) 5.43 (s, 2 H) 6.47 (d, J=8.09 Hz, 1 H) 6.97-7.06 (m, 2 H) 7.19-7.26 (m, 1 H) 7.28-7.37 (m, 3 H) 7.39-7.46 (m, 2 H) 7.68 (s, 1 H). MS (ESI), m/z 398.1 (M+1)$^+$.

Example 11 methyl 1-{4-[2-(4-methoxyphenoxy)-1,3-thiazol-5-yl]phenyl}ethylcarbamate

Example 11A 2-(4-methoxyphenoxy)-1,3-thiazole

A mixture of 4-methoxyphenol (5.50 g, 44.3 mmol, 1.1 eq.), 2-bromothiazole (6.64 g, 40.0 mmol, 1.0 eq.), and $K_2CO_3$ (6.60 g, 47.8 mmol, 1.2 eq.) in dimethyl sulfoxide (40 mL) was heated to 160° C. for 5 hours. The reaction mixture was poured into water and extracted with ether. The ether layer washed with 10% NaOH, then brine, dried over MgSO$_4$, filtered and concentrated. The residue was purified on silica gel eluting with ethyl acetate:hexane (0-20%) to give the title compound (6.03 g, 73%),

Example 11B 2-(4-methoxyphenoxy)-5-(tributylstannyl)-1,3-thiazole

To a solution of Example 11A (3.27 g, 15.8 mmol) in tetrahydrofuran (30 mL) was added n-butyl lithium (2.5 M in hexanes, 6.50 mL, 16.3 mmol, 1.0 eq.) at −78° C. The mixture was stirred for 1 hour. Tributyltin chloride (4.40 mL, 16.3 mmol, 1.0 eq) was then added at −78° C. (The dry ice bath was removed and the mixture was stirred for 1 hour. The reaction was quenched with water (100 mL). The aqueous layer was extracted with ether and the organic layer washed with brine, dried over MgSO$_4$ and concentrated. The residue was purified on silica gel eluting with ethyl acetate: hexane gradient (0-20%) to give the title compound (7.07 g, 92%).

Example 11C 2-(1-{4-[2-(4-methoxyphenoxy)-1,3-thiazol-5-yl]phenyl}ethyl)-1H-isoindole-1,3(2H)-dione To a solution of Example 11B (2.21 g, 4.45 mmol) and Example 1D (1.47 g, 4.45 mmol, 1.0 eq.) in N,N-dimethylformamide (10 mL) was added tetrakis(triphenylphosphine) palladium(0) (500 mg, 0.43 mmol, 10%). The mixture was stirred overnight at 60° C. The mixture was then poured into water. The aqueous layer was extracted with an ethyl acetate/ether mixture, which washed with water, brine, and then concentrated. The residue was purified on silica gel eluting with ethyl acetate:hexane gradient (0-50%) to give the title compound (1.56 g, 77%).

Example 11D

1-{4-[2-(4-methoxyphenoxy)-1,3-thiazol-5-yl]phenyl}ethanamine

To a solution of Example 11C (770 mg, 1.69 mmol) in methylene chloride (20 mL) and ethanol (2 min) was added hydrazine monohydrate (540 μL, 11.1 mmol, 6.6 eq.) at room temperature. The mixture was stirred at room temperature overnight. The mixture was filtered. The filtrate was concentrated. The residue was dissolved in methylene chloride again, which was filtered and the filtrate was concentrated to give the title compound (615 mg), which was used without further purification.

Example 11E methyl 1-{4-[2-(4-methoxyphenoxy)-1,3-thiazol-5-yl]phenyl}ethylcarbamate To a solution of Example 11D ((110 mg, 0.337 mmol) and diisopropylethylamine (0.5 mL) in methylene chloride (1 mL) cooled to 0° C. was added methyl chloroformate (67 μL, 0.76 mmol, 2.3 eq.). The mixture was stirred at room temperature overnight. The reaction mixture was purified directly on silica gel eluting with an ethyl acetate/hexane gradient (0-30%) to give the title compound (112 mg, 86%). $^1$H NMR (300 MHz, CDCl$_3$) δ ppm 7.35-7.45 (m, 3 H), 7.27-7.33 (m, 2 H), 7.21-7.26 (m, 2 H), 6.91-7.01 (m, 2 H), 4.73-498 (m, 1 H), 3.83 (s, 3 H), 3.66 (s, 3 H); 1.47 (d, J=6.62 Hz, 3 H) MS (DCI): m/e 385 (M+H).

Example 12

N-(1-{4-[2-(4-methoxyphenoxy)-1,3-thiazol-5-yl]phenyl}ethyl)urea

To a solution of Example 11D ((110 mg, 0.337 mmol) in methylenie chloride (1 mL) cooled to 0° C. was added trichloroacetyl isocyanate (50 μL, 0.42 mmol, 1.2 eq.). The mixture was stirred at 0° C. for 10 minutes and then methanol (10 mL) and a catalytic amount of Na$_2$CO$_3$ were added. The mixture was stirred at room temperature for 5 hours. The reaction was then concentrated. The reaction mixture was purified on silica gel eluting with ethyl acetate:hexane gradient (0-80%) to give the title compound (42 mg, 34%). $^1$H NMR (300 MHz, DMSO-$d_6$) δ ppm 7.66 (s, 1 H), 7.45-7.53 (m, 2 H), 7.32-7.40 (m, 2 H), 7.28-7.31 (m, 2 H), 7.02-7.06 (m, 2 H), 6.44 (d, J=8.09 Hz, 1 H), 5.42 (s, 2 H), 4.59-4.77 (m, 1 H), 3.79 (s, 3 H), 1.29 (d, J=6.99 Hz, 3 H); MS (DCI) m/z 370 (M+H).

Example 13

N-(1-{4-[2-(4-methoxyphenoxy)-1,3-thiazol-5-yl]phenyl}ethyl)acetamide

To a solution of Example 11D ((110 mg, 0.337 mmol) and diisopropylethylamine (0.5 mL) in methylene chloride (1 mL) cooled to 0° C. was added acetic anhydride (100 μL, 1.06 mmol, 3.1 eq.). The mixture was stirred at room temperature overnight. The reaction mixture was purified directly on silica gel eluting with ethyl acetate:hexane gradient (0-80%) to give the title compound (109 mg, 88%). $^1$H NMR (300 MHz, DMSO-$d_6$) δ ppm 8.30 (d, J=8.09 Hz, 1 H), 7.66 (s, 1 H), 7.45-7.54 (m, 2 H), 7.33-7.40 (m, 2 H), 7.27-7.32 (m, Hz, 2 H), 6.99-7.10 (m, 2 H), 4.77-4.96 (m, 1 H), 3.79 (s, 3 H), 1.83 (s, 3 H), 1.32 (d, J=6.99 Hz, 3 H); MS (DCl) m/e 369 (M+H).

It is understood that the foregoing detailed description and accompanying examples are merely illustrative and are not to be taken as limitations upon the scope of the invention, which is defined solely by the appended claims and their equivalents, Various changes and modifications including, but not limited to, those relating to the chemical structures, substituents, derivatives, intermediates, syntheses, formulations and/or methods of use of the invention, can be made without departing from the spirit and scope thereof.

We claim:
1. A compound of formula (I)

(I)

or a pharmaceutically acceptable salt, thereof, wherein
Y is selected from the group consisting of —O— and —S—;
$Ar_1$ is thiazolyl
$Ar_3$ is

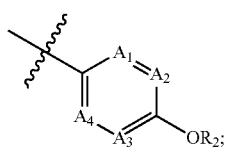
(f)

$A_1$, $A_2$, $A_3$ and $A_4$ are —C($R_v$)—, wherein $R_v$ is selected from the group consisting of hydrogen, alkyl, alkenyl, CN, $NO_2$, halogen, hydroxy, alkoxy, —$NH_2$, —N(H)alkyl, —N(alkyl)$_2$, —SH, —S(alkyl), —S(O)$_2$alkyl, —S(O)$_2$Oalkyl, —C(O)OH, —C(O)Oalkyl, —C(O)H, haloalkyl, cyanoalkyl, nitroalkyl, hydroxyalkyl, alkoxyalkyl and haloalkoxyalkyl;
$R_2$, at each occurrence, is independently selected from the group consisting of hydrogen, alkyl, alkenyl, haloalkyl, alkoxyalkyl, haloalkoxyalkyl, —$R_4$, and -alkylenyl-$R_4$;
$R_4$, at each occurrence, is independently selected from the group consisting of aryl, heteroaryl, heterocycle, cycloalkyl and cycloalkenyl;
$Ar_2$ is a group of formula (a) or (b);

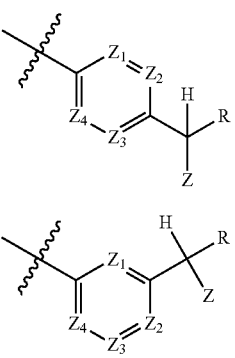
(a)

(b)

wherein
R is hydrogen, cycloalkyl, alkyl or haloalkyl;
$Z_1$, $Z_2$, $Z_3$ and $Z_4$ are C($R_{101}$), or one or two of $Z_1$, $Z_2$, $Z_3$ and $Z_4$ is N and the others are C($R_{101}$);

$R_{101}$, at each occurrence, is independently hydrogen, alkyl, alkenyl, halogen, —CN, —$NO_2$, hydroxy, alkoxy, —$NH_2$, —N(H)(alkyl), —N(alkyl)$_2$, —C(O)OH, —C(O)Oalkyl, —C(O)H, —C(O)alkyl, or haloalkyl;
Z is selected from the group consisting of —$OR_5$, -alkylenyl-$OR_5$, —N($R_6$)($R_7$) and -alkylenyl-N($R_6$)($R_7$);
$R_5$, at each occurrence, is independently selected from the group consisting of hydrogen, alkyl, haloalkyl, $R_4$, —C(O)$OR_8$, —S(O)$_2R_8$, —C(O)N($R_9$)($R_{10}$), —S(O)$_2$N($R_9$)($R_{10}$), —C(O)$R_8$, -alkylenyl-$OR_8$, -alkylenyl-N($R_9$)($R_{10}$), -alkylenyl-N($R_9$)C(O)$OR_8$, -alkylenyl-N($R_9$)C(O)$R_8$, -alkylenyl-C(O)$OR_9$, -alkylenyl-S(O)$_2R_8$, -alkylenyl-S(O)$_2$N($R_9$)($R_{10}$), -alkylenyl-C(O)N($R_9$)($R_{10}$), -alkylenyl-C(O)$R_8$, and -alkylenyl-$R_4$,
$R_6$, at each occurrence, is independently selected from the group consisting of hydrogen, alkyl and haloalkyl;
$R_7$, at each occurrence, is independently selected from the group consisting of hydrogen, alkyl, hydroxy, alkoxy, $R_4$, —C(=NH)$NH_2$, —C(O)$OR_8$, —S(O)$_2R_8$, —C(O)N($R_9$)($R_{11}$), —C(O)ON($R_9$)($R_{11}$), —S(O)$_2$N($R_9$)($R_{11}$), —C(O)$R_8$, —C(O)$CH_2$C(O)$R_8$, haloalkyl, -alkylenyl-$OR_8$, -alkylenyl-N($R_9$)($R_{11}$), -alkylenyl-N($R_9$)C(O)$OR_8$, -alkylenyl-N(R))C(O)$R_8$, -alkylenyl-C(O)$OR_8$, -alkylenyl-S(O)$_2R_8$, -alkylenyl-S(O)$_2$N($R_9$)($R_{11}$), -alkylenyl-C(O)N($R_9$)($R_{11}$), -alkylenyl-C(O)$R_8$, and -alkylenyl-$R_4$,
$R_8$, at each occurrence, is independently selected from the group consisting of hydrogen, alkyl, alkoxyalkyl, cyanoalkyl, haloalkyl, —$R_4$, and -alkylenyl-$R_4$;
$R_9$, at each occurrence, are each independently selected from the group consisting of hydrogen, alkyl and haloalkyl;
$R_{10}$, at each occurrence, is independently selected from the group consisting of hydrogen, alkyl, hydroxy, alkoxy, alkoxyalkyl, cyanoalkyl, haloalkyl, —$R_4$, and -alkylenyl-$R_4$;
$R_{11}$, at each occurrence, is independently selected from the group consisting of hydrogen, alkyl, hydroxy, alkoxy, —$R_4$, alkoxyalkyl, cyanoalkyl, haloalkyl, -alkylenyl-C(O)$NH_2$, -alkylenyl-C(O)N(H)(alkyl), -alkylenyl-C(O)N(alkyl)$_2$, -alkylenyl-N(H)C(O)Oalkyl, -alkylenyl-N(alkyl)C(O)Oalkyl, and -alkylenyl-$R_4$; and
the cycloalkyl, cycloalkenyl, aryl, heteroaryl, and heterocycle represented by $R_4$, are each independently unsubstituted or substituted with 1, 2, 3 or 4 substituents independently selected from the group consisting of alkyl, alkenyl, —CN, —$NO_2$, halogen, ethylenedioxy, methylenedioxy, oxo, —$OR_a$, —OC(O)$R_a$, —OC(O)$OR_a$, —OS(O)$_2R_a$, —S(alkyl), —S(O)alkyl, —S(O)$_2$alkyl, —S(O)$_2OR_a$, —S(O)$_2NR_aR_b$, C(O)$R_a$, —C(O)$NR_aR_b$, —C(O)$OR_a$, —C(O)$NR_aR_b$, —$NR_aR_b$, —$NOR_a$, —N($R_b$)C(O)$R_a$, —N($R_b$)C(O)$OR_a$, —N($R_b$)S(O)$_2R_a$, —N($R_b$)C(O)$NR_aR_b$, —N($R_b$)S(O)$_2NR_aR_b$, haloalkyl, cyanoalkyl, nitroalkyl, hydroxyalkyl, alkoxyalkyl, haloalkoxyalkyl, -alkylenyl-OC(O)$R_3$, -alkylenyl-OC(O)$OR_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2OR_a$, -alkylenyl-S(O)$_2NR_aR_b$, -alkylenyl-C(O)$R_a$, -alkylenyl-C(O)$NR_aR_b$, -alkylenyl-C(O)$OR_a$, -alkylenyl-C(O)$NR_aR_b$, -alkylenyl-$NR_aR_b$, -alkylenyl-N($R_b$)C(O)$R_a$, -alkylenyl-N($R_b$)C(O)$OR_a$, -alkylenyl-N($R_b$)S(O)$_2R_a$, -alkylenyl-N($R_b$)C(O)$NR_aR_b$, and -alkylenyl-N($R_b$)S(O)$_2NR_aR_b$; wherein $R_a$ at each occurrence is independently selected from the group consisting of hydrogen, alkyl, alkenyl and haloalkyl, and $R_b$ at each occurrence is independently selected from the group consisting of hydrogen and alkyl.

2. The compound of claim 1 or a pharmaceutically acceptable salt, thereof, wherein
Y is O; and
$Ar_2$ is

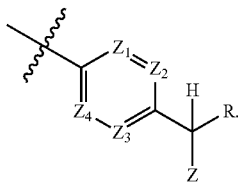
(a)

3. The compound of claim 2 or a pharmaceutically acceptable salt, thereof, wherein
$R_2$ is alkyl;
R is alkyl or haloalkyl; and
Z is $N(R_6)(R_7)$; wherein $R_6$ is hydrogen or alkyl, and $R_7$ is selected from the group consisting of —C(O)Oalkyl, —C(O)NH$_2$, —C(O)N(H)(alkyl) and —C(O)alkyl.

4. The compound of claim 2 or a pharmaceutically acceptable salt, thereof, wherein
$R_v$ is selected from the group consisting of hydrogen, —I, —Br, —Cl, and —F;
$R_2$ is selected from the group consisting of methyl, ethyl, isopropyl, and 2-methylpropyl;
$R_{101}$ is hydrogen, methyl or ethyl;
R is methyl or trifluoromethyl; and
Z is $N(R_6)(R_7)$; wherein $R_6$ is hydrogen or methyl, and $R_7$ is selected from the group consisting of —C(O)O-methyl, —C(O)NH$_2$, —C(O)N(H)(methyl); and —C(O) methyl.

5. The compound of claim 4 selected from the group consisting of:
N-(1-{4-[2-(4-isopropoxyphenoxy)-1,3-thiazol-5-yl]phenyl}ethyl)acetamide;
N-(1-{4-[2-(4-isopropoxyphenoxy)-1,3-thiazol-5-yl]phenyl}ethyl)urea;
methyl 1-{4-[2-(4-methoxyphenoxy)-1,3-thiazol-5-yl]phenyl}ethylcarbamate;
N-(1-{4-[2-(4-methoxyphenoxy)-1,3-thiazol-5-yl]phenyl}ethyl)urea; and
N-(1-{4-[2-(4-methoxyphenoxy)-1,3-thiazol-5-yl]phenyl}ethyl)acetamide;
or a pharmaceutically acceptable salt, thereof.

6. The compound of claim 1 or a pharmaceutically acceptable salt, thereof, wherein
Y is O; and
$Ar_2$ is

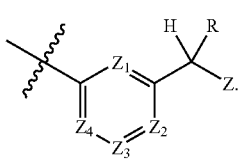
(b)

7. The compound of claim 6 or a pharmaceutically acceptable salt, thereof, wherein
$R_2$ is alkyl;
R is alkyl or haloalkyl; and
Z is $N(R_6)(R_7)$; wherein $R_6$ is hydrogen or alkyl, and $R_7$ is selected from the group consisting of —C(O)Oalkyl, —C(O)NH$_2$, —C(O)N(H)(alkyl) and —C(O)alkyl.

8. The compound of claim 6 or a pharmaceutically acceptable salt, thereof, wherein
$R_v$ is selected from the group consisting of hydrogen, —I, —Br, —Cl, and —F;
$R_2$ is selected from the group consisting of methyl, ethyl, isopropyl, and 2-methylpropyl;
$R_{101}$ is hydrogen, methyl or ethyl;
R is methyl or trifluoromethyl; and
Z is $N(R_6)(R_7)$; wherein $R_6$ is hydrogen or methyl, and $R_7$ is selected from the group consisting of —C(O)O-methyl, —C(O)NH$_2$, —C(O)N(H)(methyl); and —C(O) methyl.

9. The compound of claim 8 selected from the group consisting of:
N-(1-{5-[2-(4-isopropoxyphenoxy)-1,3-thiazol-5-yl]pyridin-3-yl}ethyl)acetamide;
methyl 1-{5-[2-(4-isopropoxyphenoxy)-1,3-thiazol-5-yl]pyridin-3-yl}ethylcarbamate;
N-(1-{5-[2-(4-isopropoxyphenoxy)-1,3-thiazol-5-yl]pyridin-3-yl}ethyl)-N'-methylurea;
N-(1-{3-[2-(4-isopropoxyphenoxy)-1,3-thiazol-5-yl]phenyl}ethyl)acetamide;
methyl 1-{3-[2-(4-isopropoxyphenoxy)-1,3-thiazol-5-yl]phenyl}ethylcarbamate;
N-(1-{3-[2-(4-isopropoxyphenoxy)-1,3-thiazol-5-yl]phenyl}ethyl) —N'-methylurea; and
N-(1-{3-[2-(4-isopropoxyphenoxy)-1,3-thiazol-5-yl]phenyl}ethyl)urea;
or a pharmaceutically acceptable salt, thereof.

10. A method of inhibiting ACC comprising administering to a patient in need thereof a therapeutically effective amount of a compound of claim 1.

11. A method of inhibiting ACC-1 comprising administering to a patient in need thereof a therapeutically effective amount of a compound of claim 1.

12. A method of inhibiting ACC-2 comprising administering to a patient in need thereof a therapeutically effective amount of a compound of claim 1.

13. A method of treating metabolic syndrome comprising administering to a patient in need thereof a therapeutically effective amount of a compound of claim 1.

14. A method of treating type II diabetes comprising administering to a patient in need thereof a therapeutically effective amount of a compound of claim 1.

15. A method of treating obesity comprising administering to a patient in need thereof a therapeutically effective amount of a compound of claim 1.

16. A pharmaceutical composition comprising a therapeutically effective amount of a compound of claim 1 in combination with a pharmaceutically acceptable carrier.

* * * * *